(12) United States Patent
Eagleman et al.

(10) Patent No.: US 11,644,900 B2
(45) Date of Patent: *May 9, 2023

(54) METHOD AND SYSTEM FOR PROVIDING ADJUNCT SENSORY INFORMATION TO A USER

(71) Applicant: NeoSensory, Inc., Houston, TX (US)

(72) Inventors: David M. Eagleman, Houston, TX (US); Scott D. Novich, Houston, TX (US); Danny Goodman, Houston, TX (US); Abhipray Sahoo, Houston, TX (US); Michael Perrotta, Houston, TX (US)

(73) Assignee: NeoSensory, Inc., Palo Alto, CA (US)

( * ) Notice: Subject to any disclaimer, the term of this patent is extended or adjusted under 35 U.S.C. 154(b) by 19 days.

This patent is subject to a terminal disclaimer.

(21) Appl. No.: 17/357,679

(22) Filed: Jun. 24, 2021

(65) Prior Publication Data

US 2021/0318757 A1  Oct. 14, 2021

Related U.S. Application Data

(63) Continuation of application No. 16/817,300, filed on Mar. 12, 2020, now Pat. No. 11,079,851, which is a
(Continued)

(51) Int. Cl.
*G06F 3/01* (2006.01)
*G08B 6/00* (2006.01)
(Continued)

(52) U.S. Cl.
CPC .......... *G06F 3/016* (2013.01); *A61F 11/045* (2013.01); *G08B 1/08* (2013.01); *G08B 6/00* (2013.01);
(Continued)

(58) Field of Classification Search
None
See application file for complete search history.

(56) References Cited

U.S. PATENT DOCUMENTS

| 3,342,923 A | 9/1967 | Henley |
| 4,255,801 A | 3/1981 | Ode et al. |
| 4,354,064 A | 10/1982 | Scott |
| 4,581,491 A | 4/1986 | Boothroyd |

(Continued)

FOREIGN PATENT DOCUMENTS

| CN | 104011794 A | 8/2014 |
| CN | 105739674 A | 7/2016 |

(Continued)

OTHER PUBLICATIONS

Conlon, Brendan , et al., "Biomodal neuromodulation combining sound and tongue stimulation reduces tinnitus symptoms in a large randomized clinical study", Science Translational Medicine, Research Article, 12, eabb2830 (2020) Oct. 7, 2020.
(Continued)

*Primary Examiner* — Fekadeselassie Girma
(74) *Attorney, Agent, or Firm* — Jeffrey Schox; Caitlin Ploch

(57) ABSTRACT

A method for providing information to a user, the method including: receiving an input signal from a sensing device associated with a sensory modality of the user; generating a preprocessed signal upon preprocessing the input signal with a set of preprocessing operations; extracting a set of features from the preprocessed signal; processing the set of features with a neural network system; mapping outputs of the neural network system to a device domain associated with a device including a distribution of haptic actuators in proximity to the user; and at the distribution of haptic actuators, coop-
(Continued)

eratively producing a haptic output representative of at least a portion of the input signal, thereby providing information to the user.

20 Claims, 10 Drawing Sheets

Related U.S. Application Data continuation of application No. 16/223,986, filed on Dec. 18, 2018, now Pat. No. 10,642,362, which is a continuation of application No. 15/696,997, filed on Sep. 6, 2017, now Pat. No. 10,198,076.

(60) Provisional application No. 62/384,036, filed on Sep. 6, 2016.

(51) Int. Cl.
*G09B 21/04* (2006.01)
*A61F 11/04* (2006.01)
*G10L 15/16* (2006.01)
*G10L 21/16* (2013.01)
*G08B 1/08* (2006.01)
*G10L 15/14* (2006.01)

(52) U.S. Cl.
CPC .............. *G09B 21/04* (2013.01); *G10L 15/16* (2013.01); *G10L 21/16* (2013.01); *G10L 15/144* (2013.01)

(56) References Cited

U.S. PATENT DOCUMENTS

| | | | |
|---|---|---|---|
| 4,665,494 A | 5/1987 | Tanaka et al. | |
| 4,926,879 A * | 5/1990 | Sevrain | G08B 6/00 340/407.1 |
| 5,553,148 A | 9/1996 | Werle | |
| 5,655,271 A | 8/1997 | Maxwell-Trumble et al. | |
| 6,027,463 A | 2/2000 | Moriyasu | |
| 6,155,971 A | 12/2000 | Calhoun et al. | |
| 6,155,995 A | 12/2000 | Lin | |
| 6,272,466 B1 * | 8/2001 | Harada | G06V 40/16 704/271 |
| 6,295,703 B1 | 10/2001 | Adams et al. | |
| 6,671,618 B2 | 12/2003 | Hoisko | |
| 7,146,218 B2 | 12/2006 | Esteller et al. | |
| 7,222,075 B2 | 5/2007 | Petrushin | |
| 7,232,948 B2 | 6/2007 | Zhang | |
| 7,921,069 B2 | 4/2011 | Canny et al. | |
| 7,979,146 B2 * | 7/2011 | Ullrich | G06F 3/016 340/407.1 |
| 8,005,681 B2 | 8/2011 | Hovestadt et al. | |
| 8,068,025 B2 * | 11/2011 | Devenyi | H04R 1/1041 340/407.1 |
| 8,588,464 B2 | 11/2013 | Albertson et al. | |
| 8,724,841 B2 | 5/2014 | Bright et al. | |
| 8,754,757 B1 * | 6/2014 | Ullrich | G08B 6/00 340/407.1 |
| 8,952,888 B2 | 2/2015 | Van Den Eerenbeemd et al. | |
| 9,019,087 B2 * | 4/2015 | Bakircioglu | H04N 21/43074 340/407.1 |
| 9,064,387 B2 | 6/2015 | Bhatia et al. | |
| 9,104,271 B1 | 8/2015 | Adams et al. | |
| 9,124,979 B2 | 9/2015 | Ogrady et al. | |
| 9,147,328 B2 | 9/2015 | Ioffreda et al. | |
| 9,298,260 B2 * | 3/2016 | Karaoguz | G06F 3/041 |
| 9,317,116 B2 | 4/2016 | Ullrich et al. | |
| 9,324,320 B1 | 4/2016 | Stolcke et al. | |
| 9,345,433 B1 | 5/2016 | Shinozuka et al. | |
| 9,368,005 B2 | 6/2016 | Cruz-Hernandez et al. | |
| 9,443,410 B1 * | 9/2016 | Constien | G08B 21/043 |
| 9,474,683 B1 | 10/2016 | Mortimer et al. | |
| 9,613,619 B2 | 4/2017 | Lev-Tov et al. | |
| 9,626,845 B2 | 4/2017 | Eagleman et al. | |
| 9,659,384 B2 | 5/2017 | Shaji et al. | |
| 9,682,232 B2 | 6/2017 | Shore et al. | |
| 9,714,075 B2 | 7/2017 | Watkins et al. | |
| 9,735,364 B2 | 8/2017 | Cheng et al. | |
| 9,760,171 B2 | 9/2017 | Cruz-Hernandez et al. | |
| 9,781,392 B2 | 10/2017 | Sahay et al. | |
| 9,905,090 B2 * | 2/2018 | Ullrich | G08B 6/00 |
| 9,987,962 B1 | 6/2018 | Salter et al. | |
| 10,258,790 B2 | 4/2019 | Guarraia et al. | |
| 10,455,320 B2 | 10/2019 | Ralph | |
| 10,497,246 B2 | 12/2019 | Arnold et al. | |
| 10,642,362 B2 * | 5/2020 | Eagleman | A61F 11/045 |
| 10,685,666 B2 | 6/2020 | Maziewski et al. | |
| 10,739,852 B2 | 8/2020 | Amstutz | |
| 2002/0090100 A1 | 7/2002 | Thiede et al. | |
| 2002/0111737 A1 | 8/2002 | Hoisko | |
| 2002/0194002 A1 | 12/2002 | Petrushin | |
| 2003/0025595 A1 | 2/2003 | Langberg | |
| 2003/0067440 A1 | 4/2003 | Rank | |
| 2003/0117371 A1 | 6/2003 | Roberts et al. | |
| 2003/0151597 A1 | 8/2003 | Roberts et al. | |
| 2003/0158587 A1 | 8/2003 | Esteller et al. | |
| 2003/0179190 A1 | 9/2003 | Franzen | |
| 2005/0113167 A1 | 5/2005 | Buchner et al. | |
| 2005/0192514 A1 | 9/2005 | Kearby et al. | |
| 2007/0041600 A1 * | 2/2007 | Zachman | A61F 11/045 381/316 |
| 2007/0242040 A1 * | 10/2007 | Ullrich | G10L 21/06 345/157 |
| 2008/0120029 A1 | 5/2008 | Zelek et al. | |
| 2008/0140422 A1 * | 6/2008 | Hovestadt | B60R 16/0373 704/E15.045 |
| 2008/0170118 A1 | 7/2008 | Albertson et al. | |
| 2009/0006363 A1 | 1/2009 | Canny et al. | |
| 2009/0012638 A1 | 1/2009 | Lou | |
| 2009/0096632 A1 * | 4/2009 | Ullrich | H04N 21/81 340/407.1 |
| 2010/0249637 A1 | 9/2010 | Walter et al. | |
| 2010/0302033 A1 * | 12/2010 | Devenyi | H04R 1/1041 381/56 |
| 2010/0318007 A1 | 12/2010 | Obrien | |
| 2011/0009921 A1 | 1/2011 | Tass et al. | |
| 2011/0061017 A1 | 3/2011 | Ullrich et al. | |
| 2011/0063208 A1 * | 3/2011 | Van Den Eerenbeemd | G06F 3/011 340/407.1 |
| 2011/0105967 A1 | 5/2011 | Zeng et al. | |
| 2011/0202155 A1 | 8/2011 | Ullrich et al. | |
| 2011/0202337 A1 | 8/2011 | Fuchs et al. | |
| 2011/0221694 A1 | 9/2011 | Karaoguz et al. | |
| 2011/0319796 A1 | 12/2011 | Campdera | |
| 2012/0023785 A1 | 2/2012 | Barnes et al. | |
| 2012/0046579 A1 | 2/2012 | Radl et al. | |
| 2012/0283593 A1 | 11/2012 | Searchfield et al. | |
| 2013/0102937 A1 | 4/2013 | Ehrenreich et al. | |
| 2013/0163797 A1 | 6/2013 | Suzman et al. | |
| 2013/0218456 A1 * | 8/2013 | Zelek | G01C 21/20 701/411 |
| 2013/0265286 A1 | 10/2013 | Da Costa et al. | |
| 2014/0064516 A1 | 3/2014 | Cruz-Hernandez et al. | |
| 2014/0176415 A1 | 6/2014 | Buuck et al. | |
| 2014/0270190 A1 | 9/2014 | Flynn et al. | |
| 2014/0350441 A1 | 11/2014 | Shafieloo | |
| 2014/0363138 A1 | 12/2014 | Coviello et al. | |
| 2015/0003635 A1 | 1/2015 | Baker et al. | |
| 2015/0025895 A1 | 1/2015 | Schildbach | |
| 2015/0038887 A1 | 2/2015 | Piccirillo | |
| 2015/0070150 A1 | 3/2015 | Levesque et al. | |
| 2015/0120289 A1 | 4/2015 | Lev-Tov et al. | |
| 2015/0126802 A1 | 5/2015 | Lim et al. | |
| 2015/0161994 A1 | 6/2015 | Tang et al. | |
| 2015/0161995 A1 | 6/2015 | Sainath et al. | |
| 2015/0227204 A1 | 8/2015 | Gipson et al. | |
| 2015/0230524 A1 | 8/2015 | Stevens et al. | |
| 2015/0241975 A1 | 8/2015 | Bhatia et al. | |
| 2015/0272815 A1 | 10/2015 | Kitchens | |

(56) References Cited

U.S. PATENT DOCUMENTS

| | | |
|---|---|---|
| 2015/0294597 A1 | 10/2015 | Rizzo |
| 2015/0305974 A1 | 10/2015 | Ehrenreich et al. |
| 2015/0351999 A1 | 12/2015 | Brouse |
| 2015/0356889 A1 | 12/2015 | Schwartz |
| 2016/0012688 A1 | 1/2016 | Eagleman et al. |
| 2016/0026253 A1* | 1/2016 | Bradski ............... H04N 13/128 345/8 |
| 2016/0027338 A1 | 1/2016 | Ebeling et al. |
| 2016/0049915 A1 | 2/2016 | Wang et al. |
| 2016/0098844 A1 | 4/2016 | Shaji et al. |
| 2016/0098987 A1 | 4/2016 | Stolcke et al. |
| 2016/0103590 A1 | 4/2016 | Vu et al. |
| 2016/0187987 A1 | 6/2016 | Ullrich et al. |
| 2016/0254454 A1 | 9/2016 | Cheng et al. |
| 2016/0255944 A1 | 9/2016 | Baranski et al. |
| 2016/0284189 A1 | 9/2016 | Constien |
| 2016/0292856 A1 | 10/2016 | Niemeijer et al. |
| 2016/0297611 A1 | 10/2016 | Williams et al. |
| 2016/0358429 A1* | 12/2016 | Ullrich .................... G08B 6/00 |
| 2016/0367190 A1 | 12/2016 | Vaitaitis |
| 2017/0169673 A1* | 6/2017 | Billington ............... H04W 4/20 |
| 2017/0206889 A1* | 7/2017 | Lev-Tov ................ G10L 15/26 |
| 2017/0213568 A1 | 7/2017 | Foshee |
| 2017/0290736 A1 | 10/2017 | Idris |
| 2017/0294086 A1 | 10/2017 | Kerdemelidis |
| 2017/0348184 A1 | 12/2017 | Pisharodi et al. |
| 2018/0033263 A1 | 2/2018 | Novich et al. |
| 2018/0210552 A1 | 7/2018 | Saboune et al. |
| 2018/0284894 A1 | 10/2018 | Raut et al. |
| 2018/0303702 A1 | 10/2018 | Novich et al. |
| 2018/0315343 A1 | 11/2018 | Shvartzberg et al. |
| 2018/0374264 A1 | 12/2018 | Gatson et al. |
| 2019/0045296 A1 | 2/2019 | Ralph |
| 2019/0201657 A1 | 7/2019 | Popelka et al. |
| 2019/0337451 A1 | 11/2019 | Bacchus et al. |
| 2019/0379977 A1 | 12/2019 | Buttner et al. |
| 2020/0121544 A1 | 4/2020 | George et al. |
| 2020/0209975 A1* | 7/2020 | Eagleman ............. A61F 11/045 |
| 2021/0089130 A1 | 3/2021 | Novich et al. |
| 2021/0110841 A1 | 4/2021 | Weber et al. |
| 2021/0169735 A1 | 6/2021 | Northen et al. |
| 2021/0325969 A1 | 10/2021 | Eagleman et al. |
| 2022/0023137 A1 | 1/2022 | Rha |
| 2022/0078566 A1 | 3/2022 | Haefeli |

FOREIGN PATENT DOCUMENTS

| | | |
|---|---|---|
| EP | 0911002 A2 | 4/1999 |
| WO | 2008106698 A1 | 9/2008 |
| WO | 2012069429 A1 | 5/2012 |
| WO | 2015028480 A1 | 3/2015 |

OTHER PUBLICATIONS

International Search Report and Written Opinion for PCT Application No. PCT/US2017/050288 dated Nov. 8, 2017.

Jones et al., Development of a Tactile Vest, 2004, IEEE, 0-7695-2112-6/04 (Year: 2004).

Nakamura et al., An Actuator for the Tactile Vest—a Torso-Based Haptic Device, 2003, IEEE, 0-7695-1890-7/03 (Year: 2003).

Paneels et al., What's Around Me? Multi-Actuator Haptic Feedback on the Wrist, Apr. 14-18, 2013, IEEE, 978-1-4799-0088-6/13, pp. 407-412 (Year: 2013).

Plant, Geoff, "Training in the use of the Tactaid VII: A case study", KTH Computer Science and Communication (STL-QPSR), 1994, vol. 35, No. 1, pp. 091-102.

Tapson et al., The Feeling of Color: A Haptic Feedback Device for the Visually Disabled, 2008, IEEE, 978-1-4244-2879-3/08, pp. 381-384 (Year: 2008).

Graves, Alex, et al., "Bidirectional LSTM Networks for Improved Phoneme Classification and Recognition", ResearchGate, Conference Paper, Jan. 2005.

Naguma, Hirofumi, et al., "Minimum Latency Training Strategies for Streaming Sequence-to-Sequence ASR", arXiv:2004.05009v2, May 15, 2020, Accepted at IEEE ICASSP 2020.

Yu, Haibao, et al., "Low-bit Quantization Needs Good Distribution", Published in: 2020 IEEE/CVF Conference on Computer Vision and Pattern Recognition Workshops (CVPRW), Jun. 14-19, 2020.

Isaac W. Experience Sound as Touch and Gain New Awarness. "Neosensory Buzz" (Neosensory) Aug. 17, 2020 (Aug. 17, 2020) [, pp. 1-14 USA https://web.archive.orghveb/20200817163453/ and https://neosensory.com/.

"The Wristband That Gives You Superpowers" (NEO.LIFE) Jan. 10, 2019 (Jan. 10, 2019) 1-16.

Horvath et al., FingerSight: Fingertip Haptic Sensing of the Visual Environment, Mar. 6, 2014, IEEE, vol. 2, 2014 (Year: 2014).

International Search Report and Written Opinion for PCT Application No. PCT/US17/58597 dated Jan. 4, 2018.

* cited by examiner

METHOD AND SYSTEM FOR PROVIDING ADJUNCT SENSORY INFORMATION TO A USER

CROSS-REFERENCE TO RELATED APPLICATIONS

This application is a continuation of U.S. patent application Ser. No. 16/817,300, filed 12 Mar. 2020, which is a continuation of U.S. patent application Ser. No. 16/223,986, filed 18 Dec. 2018, which is a continuation of U.S. patent application Ser. No. 15/696,997, filed 6 Sep. 2017, which claims the benefit of U.S. Provisional Application Ser. No. 62/384,036, filed on 6 Sep. 2016, which is incorporated in its entirety by this reference.

TECHNICAL FIELD

This invention relates generally to the sensory stimulus technology field, and more specifically to a new and useful system and method for providing information to a user.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview.

Figure 1A:
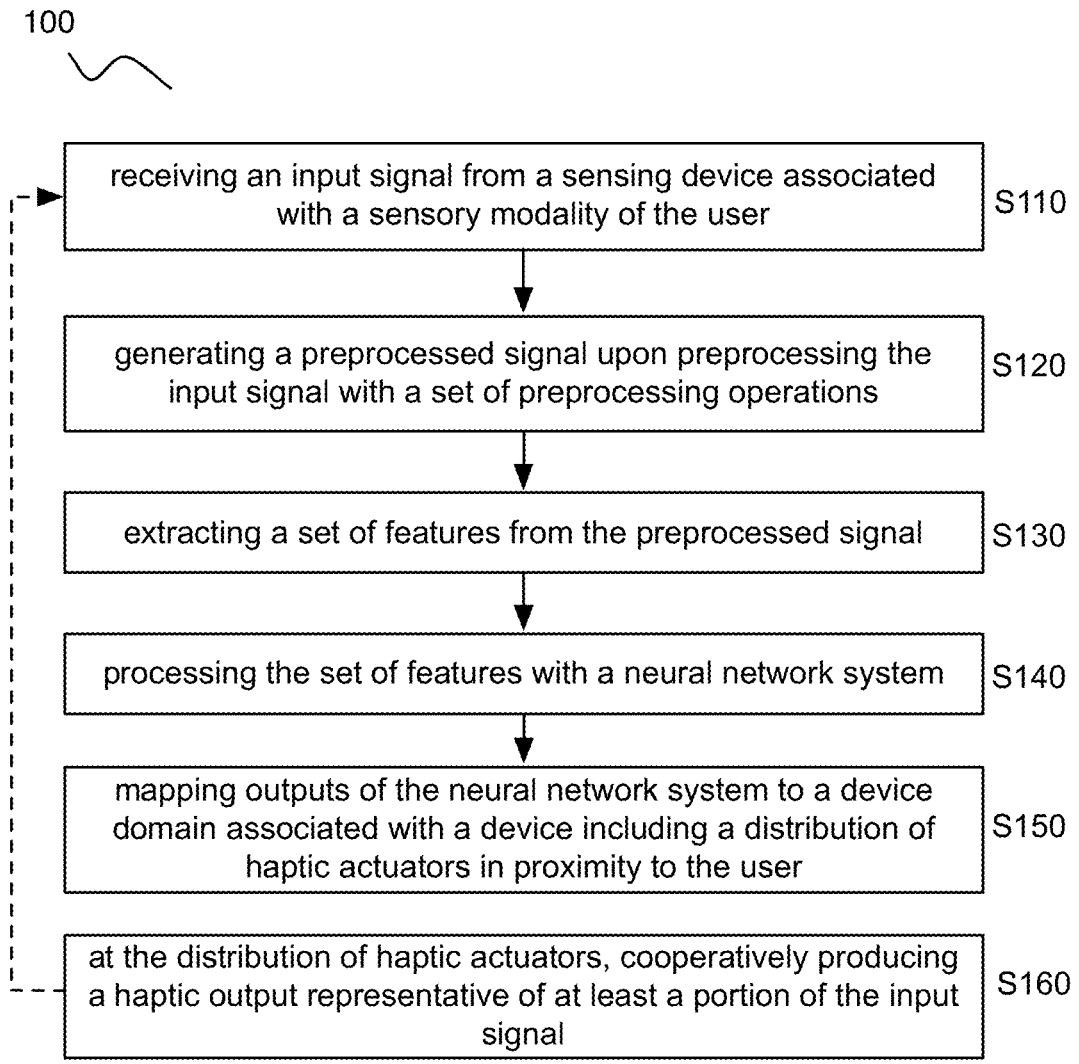
FIG. 1A is a flowchart diagram of an embodiment of the method for providing information to a user.
Figure 1B:
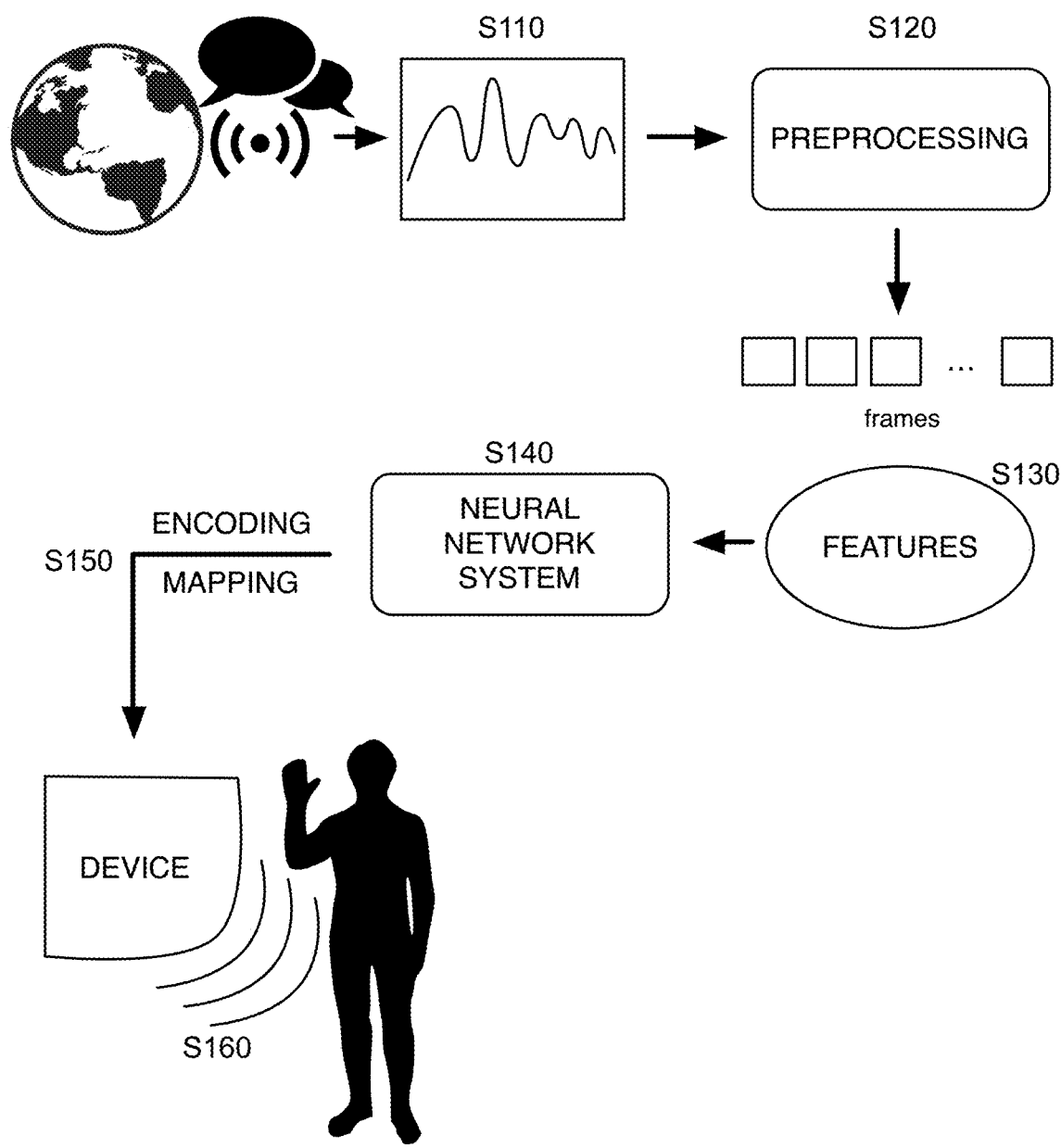
FIG. 1B is a schematic of an embodiment of a method and system for providing information to a user.

As shown in FIGS. 1A and 1B, a method 100 for providing information to a user comprises: receiving an input signal from a sensing device associated with a sensory modality of the user S110; generating a preprocessed signal upon preprocessing the input signal with a set of preprocessing operations S120; extracting a set of features from the preprocessed signal S130; processing the set of features with a neural network system S140; mapping outputs of the neural network system to a device domain associated with a device including a distribution of haptic actuators in proximity to the user S150; and at the distribution of haptic actuators, cooperatively producing a haptic output representative of at least a portion of the input signal, thereby providing information to the user S160. However, the method 100 can additionally or alternatively include any other suitable elements, and can be performed in any suitable manner.

The method 100 preferably functions to transform input signals associated with at least one sensory modality (e.g., audio signals containing communication-related information, audio signals containing other information, signals containing information associated with vision, signals containing information associated with the sensation of touch, signals containing information associated with tastes, signals containing information associated with smells, etc.) into stimuli provided using a device in proximity to or otherwise worn by a user, wherein the stimuli are associated with signal processing outputs of a different domain, dimensionality, and/or rate than the input signals. The method 100 can be used for users without sensory conditions (e.g., having sensory sensitivity within a typical range) but for whom receiving of information from multiple sensory sources is desired (e.g., to enhance perception and/or enjoyment of the information). The method 100 can additionally or alternatively allow a user with one or more sensory conditions (e.g., reduced sensory sensitivity, enhanced sensory sensitivity, lacking sensitivity in one or more sensory modalities, etc.) to receive information that would otherwise be received through the one or more senses.

In variations, the method 100 can thus operate to provide a means for sensory cross-boosting to allow a user to receive and process information, whereby sensory cross-boosting includes a conversion of a subset of information from one sensory modality (e.g., auditory information for hearing) into another sensory modality (e.g., touch). As such, sensory cross-boosting can be used as a sensory adjunct for a user or for partial sensory substitution (e.g., in relation to a user with partial sensory loss), whereby information typically associated with one sensory modality can be provided to the user by way of multiple sensory modalities of the user. Additionally or alternatively, the method can be used for sensory substitution, whereby information typically associated with one sensory modality (e.g., auditory information) is converted to stimuli associated with another sensory modality (e.g., the sensation of touch), such that the user can perceive the content of the information through a sensory modality not typically used to perceive the content of the information.

In specific examples, the method 100 can be used to provide real-time (or near real-time) understanding of information acquired using audio sensors (e.g., microphones) to a user by way of a wearable device (e.g., torso-coupled wearable device, limb-borne wearable device, head-coupled wearable device, etc.) operable to provide haptic stimuli to the user. In more detail, processing of the input signals (e.g., audio signals) can be adapted to specific demographics (e.g. age demographics, gender demographics, species demographics, etc.) or sensory conditions, and in a specific application, can include processing input audio signals to allow users with high frequency hearing loss to perceive high frequency auditory information using their sensations of touch.

The method 100 can thus be implemented using system components described in more detail below, and/or using an embodiment, variation, or example of the system described in U.S. application Ser. No. 14/750,626, titled "Providing Information to a User Through Somatosensory Feedback" and filed on 25 Jun. 2015, which is herein incorporated in its entirety by this reference. However, the method 100 can additionally or alternatively be implemented using any other suitable system or system components for providing information to users through feedback devices.

2. Benefits.

The method 100 can confer a number of benefits. First, embodiments of the method 100 can function to transform input signals with characteristic dimensionality and/or speed into stimuli (e.g., stimuli provided to a user using one or more devices as sensory inputs to the user) with different dimensionality and/or speed (e.g., transforming low-dimensionality, high-speed input information such as speech information into higher-dimensionality, lower-speed outputs such as tactile outputs; transforming high-dimensionality and/or high-speed input information into lower-dimensionality and/or lower-speed outputs; etc.). In examples, the relationship can be inversely proportional (e.g., as in sound-to-touch for speech processing, which processes a low dimensional and high speed stream into a high dimensional and low speed stream).

Second, embodiments of the method 100 can implement haptic stimuli-providing devices coupled to one or more users to provide information-rich stimuli to users, based on transformation of input signals associated with one sensory modality to stimuli associated with another sensory modality. In some embodiments, such cross-sensory transformations can aid in perception and/or understanding of the input signals, such as by supplementing and/or replacing the input signals (e.g., associated with a sensory modality for which a user has diminished sensitivity) with related (e.g., complementary, representative, etc.) information delivered via a second sensory modality (e.g., tactile sense). For example, if the input signals include information that cannot easily be provided to the user via the original sensory modality (e.g., due to sensory limitations, output device constraints, etc.), the method 100 can include providing information via the second sensory modality, enabling user perception and/or understanding of the information. In examples, such transformations can be adapted to user-specific needs associated with demographic factors (e.g., age, gender, ethnicity, etc.), health conditions, and/or any other suitable factor(s), whereby components of the information (e.g., high frequency components of speech) associated with the input signals are less readily perceived by users of interest, and stimuli provided by the devices can be modulated to fit the sensory sensitivity (e.g., haptic sensitivity) of the user. Further, in some embodiments, systems associated with such stimuli (e.g., stimulus output devices) can have beneficial form factors and/or modalities of interaction with the user(s). In a specific example, in which the method 100 includes transforming auditory input signals into haptic outputs, the haptic outputs can be provided to the user by a discretely-worn system (e.g., worn under clothing, worn on a body extremity, etc.), whereas some systems configured to provide auditory outputs may include less discrete elements.

Third, embodiments of the method 100 can decrease latency in transmitting information to a user by selecting a subset of information contained in input signals for further processing and, ultimately, transformation into stimuli provided to users, thereby improving performance of processing systems associated with the method 100.

Thus, embodiments of the method 100 can function to provide platforms and devices for supplementing and/or substituting functions of one or more sensory modalities, in a manner that is adapted to specific user needs. However, the method 100 can additionally or alternatively confer any other suitable benefits.

3. System.

Figure 2A:
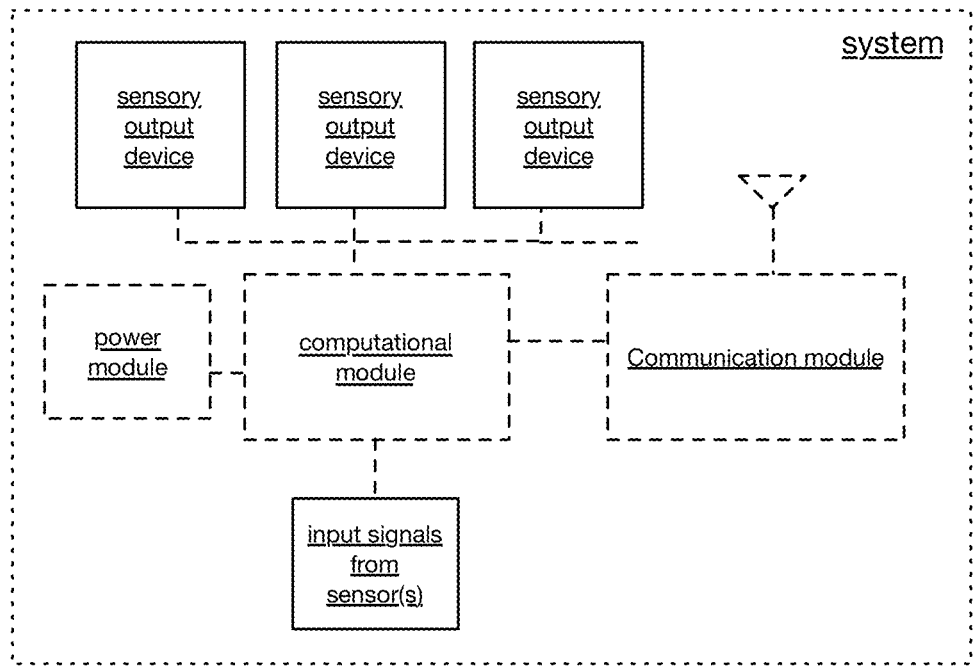
FIGS. 2A and 2B are schematics of embodiments of systems for providing information to a user.
Figure 2B:
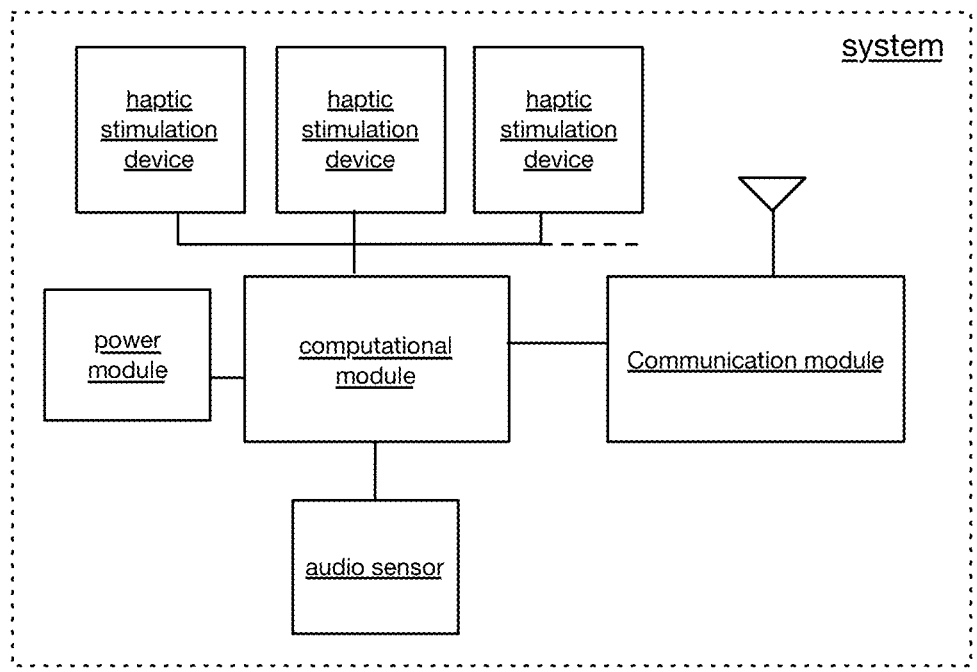

The system preferably receives or generates one or more input signals from appropriate sensors, and provides stimuli (e.g., through sensory output devices in proximity to the user), and can optionally include one or more communication modules, power modules, and/or computational modules (e.g., as shown in FIGS. 2A-2B). The device components associated with the stimuli are preferably disposed in a single device, but can additionally or alternatively be disposed across a plurality of devices, and/or be disposed in any other suitable manner.

Figure 3A:
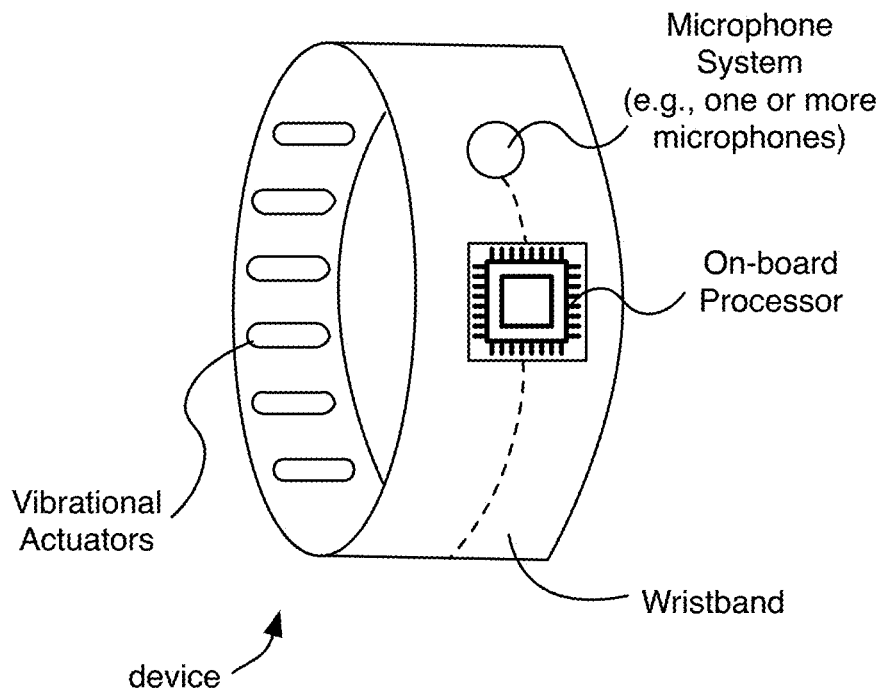
FIGS. 3A-3C depict example stimuli providing devices associated with a method and system for providing information to a user.
Figure 3B:
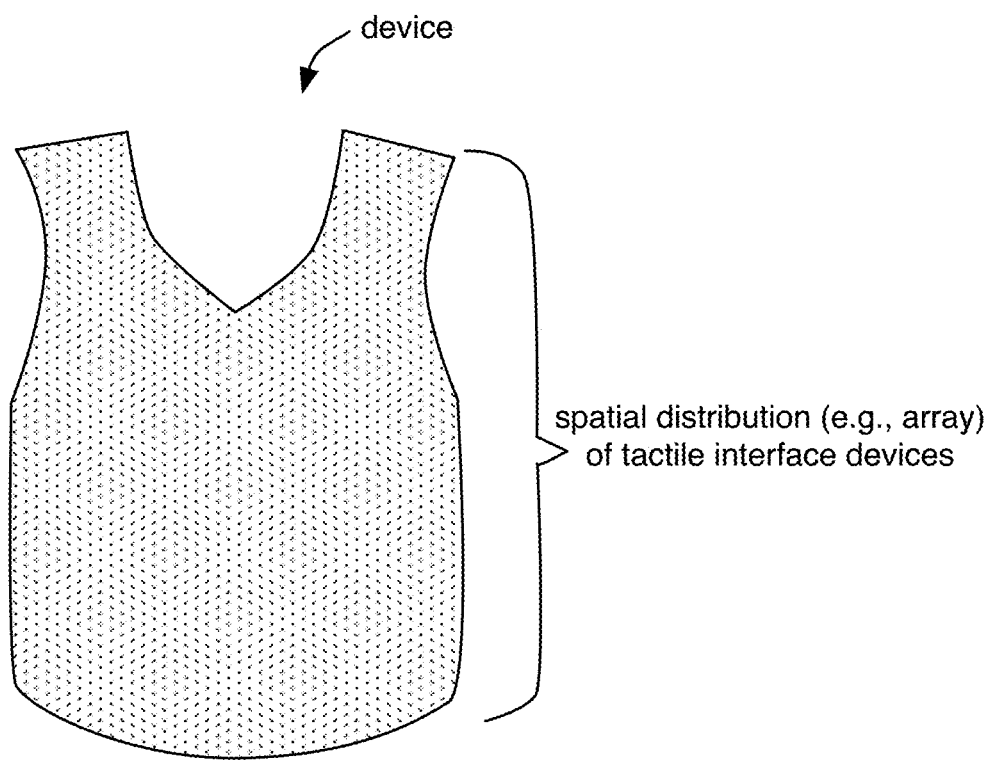

The stimuli can be provided by a plurality of tactile interface devices (e.g., haptic actuators, electrical stimulators, etc.) in a spatial distribution (e.g., multidimensional spatial distribution), each of which can provide a variety of available output stimuli with different stimulus parameters (e.g., as shown in FIGS. 3A-3B). The device(s) can provide haptic stimuli through the tactile interface devices, and in specific examples, can include an array of tactile interface devices operable to provide configurable haptic stimuli to a user. The tactile interface devices can include vibration motors (e.g., eccentric rotating mass (ERM) devices), Linear Resonant Actuators (LRAs), piezoelectric devices, and/or any other suitable devices (and/or combinations thereof, such as hybrid devices incorporating both ERM and LRA elements).

The device(s) can additionally or alternatively be operable to provide one or more of: auditory stimuli, electrical stimuli (e.g., peripheral stimuli, etc.), olfactory stimuli, taste stimuli, and any other suitable form of stimulus.

The spatial distribution (e.g., array) of tactile interface devices can have a density from 5 devices per $cm^2$ to 50 devices per $cm^2$, or any other suitable density. Furthermore, the spatial distribution of tactile interface devices can be configured with any suitable morphological aspects. The tactile interface devices are preferably arranged in one or more arrays (e.g., high-density arrays) but additionally or alternatively arrays of any suitable density. The arrays can include multidimensional arrays (e.g., planar array, 3-dimensional volumetric array, array defined substantially along one or more device surfaces, etc.), single-dimensional arrays (e.g., linear array, curvilinear array, etc.), and/or any other suitable arrays. For example, the device can include a two-dimensional array (e.g., defined substantially on a plane, defined on a curved and/or bent surface, etc.). The arrays can be configured as one or more of: a circular array, an ellipsoidal array, a polygonal array (e.g., a triangular array, rectangular array, a pentagonal array, a hexagonal array, etc.), a circumscribing array, an amorphous array, an array substantially spanning the support structure with which the array is integrated, and any other suitable array type. Additionally or alternatively, the device can include an irregular distribution of tactile interface devices (e.g., arranged substantially on a surface and/or within a volume of the device) and/or any other suitable arrangement of tactile interface devices. Furthermore, the spatial distribution (e.g., array) can be configured across different layers of the overarching device coupled to the user.

In a first embodiment, as shown in FIG. 3A, the array of tactile interface devices is integrated with a wrist-region wearable band device, wherein the array is distributed circumferentially about the band surface and coupled to electronics that facilitate provision of haptic stimuli. In this embodiment, the system comprises a housing operable to 1) contain electronics for powering the tactile interface devices and transitioning the tactile interface devices between different modes and 2) support the array of tactile interface devices while positioning the array of tactile interface devices in a manner such that the user can sense stimuli provided by the array. The housing can thus be coupled to or otherwise include a fastener that couples the system to a user. The fastener and housing can be of unitary construction or otherwise physically coextensive, or can be otherwise connected, coupled, or couplable. The fastener is preferably operable to be easily and/or repeatably fastened and unfastened manually by the user, and in specific examples, can include a latch, snap, buckle, clasp, hook-and-loop fastening mechanism, and/or any other suitable fastening mechanism, and/or can be operable to expand and contract (e.g., including an elastic element, such as an expansion band; including a deployment clasp, butterfly clasp, or other clasp that is physically coextensive when unclasped; etc.).

In a second embodiment, the tactile interface devices are configured to be carried with a user (e.g., worn by the user, in proximity to the user). In this embodiment, the tactile interface devices are preferably integrated into a wearable garment, wherein the garment can comprise a top (e.g., shirt, vest, etc.), a bottom (e.g., pants, shorts, skirt, etc.), a headpiece (e.g., headband, earmuffs, hat, etc.), a backpack, an undergarment, socks, and any other suitable form of garment. Additionally or alternatively, the tactile interface devices can be configured to be mechanically coupled to the wearable garment (e.g., retained in one or more pockets of the garment, attached by fasteners such as buttons, clips, magnets, and/or hook-and-loop fasteners, attached by adhesive, etc.). Additionally or alternatively, the tactile interface devices can be configured to attach directly to a user (e.g., by suction, adhesive, etc.), preferably to one or more skin surfaces of the user. Additionally or alternatively, the tactile interface devices can be incorporated into one or more wearable devices (e.g., a head-mounted wearable device, etc.) and/or implanted devices. Additionally or alternatively, the tactile interface devices can be incorporated into prosthetic devices (e.g., lower limb prosthetics, upper limb prosthetics, facial prosthetics, etc.). In an example, such as shown in FIG. 3B, the array of tactile interface devices can be integrated with a vest garment operable to be worn by a user as the user moves about in his/her daily life.

Figure 3C:
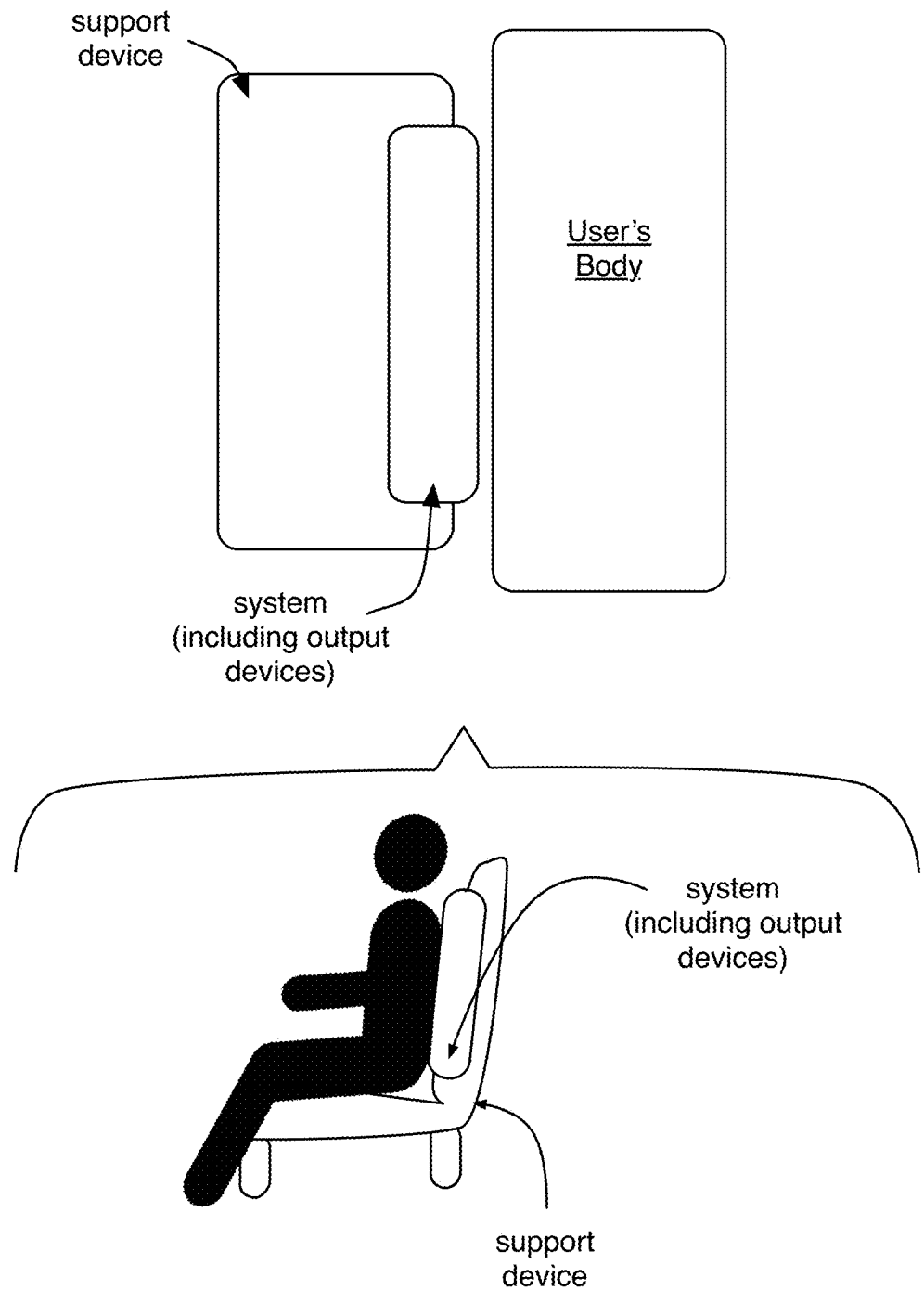

In a third embodiment, such as shown in FIG. 3C, the tactile interface devices are configured to be mechanically coupled to the user by a support device that supports the user (e.g., by a support element of the support device). For example, the tactile interface devices can be integrated into the support element and/or arranged between the user and the support element (e.g., resting on top of the support element). The support devices can include seats, couches, beds, platforms (e.g., for sitting and/or standing on), walls, inclined surfaces (e.g., configured to support a leaning user), and/or any other suitable support devices, as described in U.S. application Ser. No. 15/661,934 titled "Method and System for Determining and Providing Sensory Experiences" and filed on 27 Jul. 2017, which is herein incorporated in its entirety by this reference.

Additionally or alternatively, the tactile interface devices can be disposed in a device configured to be held by the user (e.g., hand-held, held between an arm and torso of the user, held between the legs of the user, etc.). Additionally or alternatively, the tactile interface devices can be disposed in a device configured to rest on the user (e.g., retained against the user by gravity), such as a blanket. However, the tactile interface devices can additionally or alternatively be coupleable to the user (and/or otherwise configured to interact with the user) in any other suitable manner.

Each tactile interface device (and/or other output unit) is preferably controlled by independent signals and configured to actuate independently from the other output units. Alternatively, a group of output units (e.g., a cluster or subset of the output units) can be independently controlled, such that the group of output units can operate independently from the other output units. Each controlled subset (e.g., individual output unit or cluster) can include one or more output units of the same or different types. In variations, in addition to or in alternative to controlling subsets of actuators (e.g., overlapping and/or disjoint subsets) to convey information as a function of features (e.g. in a first group for a first phoneme; in a second group, including only actuators not included in the first group, for a second phoneme; in a third group, including a subset of actuators of the first and second groups, for a third phoneme; etc.), subsets can be used to map a numerical input to a multi-actuator output. In an example, to make the impression of "sweeps" (e.g., turning actuators on and off in quick succession), one could analyze a frame of music and track the strongest/loudest frequency and control the actuators to produce upward/downward "sweeps" as a function of whether the frequency increased or decreased from a previously analyzed frame.

Each controlled subset is preferably individually identified, such that it has a locally unique identifier (e.g., index value), but can alternatively share an identifier with a second controlled subset of the device, or be otherwise identified. Each controlled subset (or the respective identifier) is preferably associated with a known, stored spatial position on the device (controlled subset position). The controlled subset position can include an arcuate position, radial position, position along an axis (e.g., lateral axis, longitudinal axis, etc.), set of coordinates, grid position, position relative to another device component (e.g., sensor, different output unit, etc.), or be any other suitable position. The controlled subset positions can be stored by the device (e.g., on volatile or non-volatile memory), can be encoded (e.g., implicitly, explicitly) via a re-indexing module (e.g., reindexing array), and/or stored (and/or otherwise made available) by any other suitable system. However, indexing and/or storing can additionally or alternatively be implemented in any other suitable manner.

Each controlled subset is preferably wired in parallel relative to other controlled subsets of the device, but can alternatively be wired in series, wired in a combination of in parallel and in series, or be wired in any other suitable manner (or not be wired). The controlled subsets of the device are preferably controlled by the processor, but can additionally or alternatively be controlled by a remote computing system (e.g., server system), external device (e.g., mobile device, appliance, etc.), and/or any other suitable computing system.

The input signals associated with the method 100 can be derived from sensors of the system 100 (e.g., wherein sensors are included with the same device(s) that provide the stimuli, wherein sensors are distinct from the devices that provide the stimuli, etc.). The input signals can be derived from local sensors (e.g., sensing an environment of the device and/or user), remote sensors (e.g., sensing a separate environment), virtual inputs (e.g., associated with a virtual environment), and/or any other suitable sensors in any other suitable configuration.

The input signals preferably include audio and/or music input signals. For example, the input signals can be derived from microphones (e.g., multiple microphones, which can be used to perform beam forming operations to remove environmental artifacts, as described below), and/or other audio sensors, sources of audio data streams (e.g., analog electrical connectors such as audio line in connectors; digital electrical and/or optical connectors configured to receive audio and/or music information such as HDMI, TOSLINK, MIDI, etc.; generic computer data connectors such as USB, Ethernet, etc.; wireless connections such as those enabled by a wireless communication module of the system; etc.), and/or any other suitable audio inputs. The sensors associated with input signals can additionally or alternatively include sensors associated with other sensory experiences (e.g., visual, tactile, olfactory, taste, etc.), other environmental information (e.g., location, location type, velocity, temperature, humidity, etc.), and/or any other suitable information.

The sensors can additionally or alternatively include one or more: cameras (e.g., CCD, CMOS, multispectral, visual range, hyperspectral, stereoscopic, etc.), spatial sensors (e.g., inertial measurement sensors, accelerometer, gyroscope, altimeter, magnetometer, etc.), location sensors (e.g., GPS, GNSS, triangulation, trilateration, etc.), audio sensors (e.g., transducer, microphone, etc.), barometers, light sensors, temperature sensors, current sensor (e.g., Hall effect sensor), air flow meter, voltmeters, touch sensors (e.g., resistive, capacitive, etc.), proximity sensors, force sensors (e.g., strain gauge meter, load cell), vibration sensors, chemical sensors, sonar sensors, and/or any other suitable sensors. However, the system can additionally or alternatively include any other suitable sensors.

The communication modules can include wired communication modules (e.g., configured to communicate by wired data connections, such as Ethernet, USB, power line, etc.) and/or wireless communication modules (e.g., radios). The wireless communication modules preferably support (e.g., enable communication using) one or more wireless communication protocols (e.g., WiFi, Bluetooth, BLE, NFC, RF, IR, Zigbee, Z-wave, etc.). However, the system can additionally or alternatively include any other suitable communication modules.

The power module can include one or more power input elements, power storage elements, and/or any other suitable elements. The power module is preferably an electrical power module with an electrical input (e.g., electrical power connection such as a wired connector or inductive loop) and/or electrical storage element (e.g., battery, supercapacitor, etc.), but can additionally or alternatively include any other suitable power input and/or storage elements. The power module can include a battery that is preferably electrically coupled (e.g., connected by conductive wires) to the powered system components, wherein the computational module preferably controls power provision (e.g., as described below), but power provision and/or battery management can additionally or alternatively be performed by any other suitable components.

The computational module can include one or more processors (e.g., CPU or other microprocessor, control circuit, relay system, etc.), computer memory modules (e.g., RAM), computer storage modules (e.g., hard disk drive, flash memory, etc.), and/or any other suitable elements. The computational module is preferably configured to control and/or receive information from the outputs, inputs, communication modules, power modules, and/or any other suitable elements of the system. The computational module can be distributed across multiple systems (e.g., remote server, personal computing device, wearable computing device, mobile computing device, etc.) and/or in the cloud, or can alternatively be implemented in a single computing system.

The computational module is preferably configured to control the controlled subsets (e.g., output units such as tactile interface devices, groups of output units, etc.) individually. In a first example, the processor is configured to provide control signals to each controlled subset (e.g., to a control element of each controlled subset, such as an actuator control circuit). Additionally or alternatively, in a second example, the processor is configured to selectively provide power from the power module to each controlled subset (e.g., by regulating the current provided to each output unit) or to selectively command each controlled subset to enter a mode or attain a set point parameter value (e.g., by communicating a command to an integrated controller of each output unit). However, the computational module can additionally or alternatively be configured to control the controlled subsets in any other suitable manner, or can be configured to not control the controlled subsets.

As described earlier, the system can include embodiments, variations, and examples of the device(s) described in U.S. application Ser. No. 14/750,626, titled "Providing Information to a User Through Somatosensory Feedback" and filed on 25 Jun. 2015; however, the system can additionally or alternatively include any other suitable devices and/or device elements.

4. Method.

4.1 Receiving Input Signals

As described in relation to the method 100 above, Block S110 recites: receiving an input signal from a sensing device associated with a sensory modality of the user. Block S110 functions to provide signals that can be transformed into stimuli provided to the user in downstream steps of the method 100. The input signals are preferably received by and/or derived from one or more sensors of the system described in Section 3 above. In particular, the input signals can be received from sensors of the system (e.g., information sampled by the sensors), other sensors (e.g., sensors connected to the system, such as by a communication module), computing systems (e.g., from computer storage, generated by the computing system, etc.), other systems, and/or any other suitable source.

The input signals can capture information associated with one or more sensory modalities (e.g., audio, visual, tactile, olfactory, etc.), and/or any other information associated with (e.g., indicative and/or representative of, sampled based on, etc.) a sensory experience (e.g., associated with the environment of the system and/or user, a remote environment, a virtual environment, etc.). The input signals can additionally or alternatively capture non-sensory information, such as information associated with an environment (e.g., the environment of the system and/or user, a remote environment, a virtual environment, etc.). For example, the input signals can include location, speed, acceleration, orientation (e.g., relative to a reference orientation and/or position of the user or of a vehicle occupied by the user), electric and/or magnetic field information (e.g., intensity, orientation, gradient, curl, etc.), navigation information (e.g., turn-by-turn directions), and/or any other suitable information, as described in relation to system components in Section 3 above.

The input signals received in Block S110 preferably include current information (e.g., sent in near real-time to the system, such as streamed substantially concurrent with sampling). The input signals received in Block S110 can additionally or alternatively include advance information (e.g., associated with a sensory experience that is expected to occur at a later time, preferably along with the expected time of occurrence), but can additionally or alternatively include historical information and/or information associated with any other suitable time (or no time).

In a first variation, Block S110 includes receiving audio signals (e.g., from a microphone system, etc.) derived from entities and/or objects in a user's environment. In this variation, receiving the audio signals can include sampling audio information at one or more microphones of a system coupled to a user or otherwise in proximity to the user, as described in relation to the system embodiments of Section 3 above, wherein using signals from multiple microphones can be used in downstream processing steps, as described in more detail below.

In one example, the audio signals can capture human communication content, from which speech components (e.g., phonetic components, etc.) can be processed, extracted, and transformed to provide stimuli to users, wherein the stimuli convey speech information (or information derived from the communication information) to the user through another sensory modality. In another example, the audio signals can capture communication from a non-human entity, from which communication components can be processed, extracted, and transformed to provide stimuli to users, wherein the stimuli convey information to the user through another sensory modality. In another example, the audio signals can capture non-communication information associated with entities or objects in the user's environment, from which features can be processed, extracted, and transformed to provide stimuli to users, wherein the stimuli convey information (or information derived from the speech information) to the user through another sensory modality. In a first specific example of this example, information can be associated with environmental hazards (e.g., alarms, vehicle traffic, hazardous conditions in proximity to the user), notifications (e.g., door bell rings, appliance notifications, etc.), and/or any other suitable environmental information that would be useful for the user to perceive. In a second specific example, information can be associated with a continuous representation of environmental sounds (e.g., associated with features such as sound frequency).

In variations, the audio signals can be received as an analog electrical representation (e.g., line in), a digital audio encoding (e.g., computer audio stream or file), and/or in any other suitable form. In these variations, Block S110 can additionally or alternatively include receiving timing information associated with the audio information (e.g., synchronization information, such as the time at which a portion of the audio information was captured from the user's environment, etc.). However, Block S110 can additionally or alternatively receiving any other suitable input information (e.g., olfactory stimuli, taste stimuli, etc.) in any other suitable manner.

4.2 Preprocessing Input Signals

Block S120 recites: generating a preprocessed signal upon preprocessing the input signal with a set of preprocessing operations, which functions to process out undesired signal components from the input signal(s) received in Block S110, and/or perform suitable preprocessing operations on the input signal to facilitate downstream portions of the method 100. Block S120 is preferably implemented at the processing system components in communication or otherwise coupled to the sensor components associated with Block S110 and described in Section 3 above; however, Block S120 can additionally or alternatively be implemented using any other suitable system components.

In variations, Block S120 can include filtering out signal components associated with noise and/or attenuating or accentuating signal components in any other suitable manner, in order to increase the signal-to-noise ratio (SNR) of input signal(s). Block S120 can additionally or alternatively include filtering or otherwise processing frequency components of the input signal associated with or not associated with specific hearing conditions of the user(s) involved. For example, Block S120 can include isolating high frequency components of the input signals for downstream processing according to subsequent blocks of the method 100, in order to provide information to users with high frequency hearing loss. In more detail, isolation of frequency components (or ranges of frequency components) can implement an algorithm that prioritizes features of interest to the user (e.g., based on sensory condition details, based on typical user preferences, based on personal interest, based on professional interests, etc.) or de-prioritizes features not of interest to the user (e.g., for a user lacking auditory sensitivity in a high-frequency band but having strong auditory sensitivity in a low-frequency band, including many or all features associated with inputs in the high-frequency band but excluding some or all features associated with inputs in the low-frequency band). However, Block S120 can include post-processing or pre-processing the feature sets in any other suitable manner.

In variations, Block S120 can implement one or more digital techniques including one or more of: of an infinite impulse response (IIR) filter, a finite impulse response (FIR) filter, high pass filter, a low pass filter, and a band pass filter operation for processing signals in frequency ranges of interest.

Figure 4A:
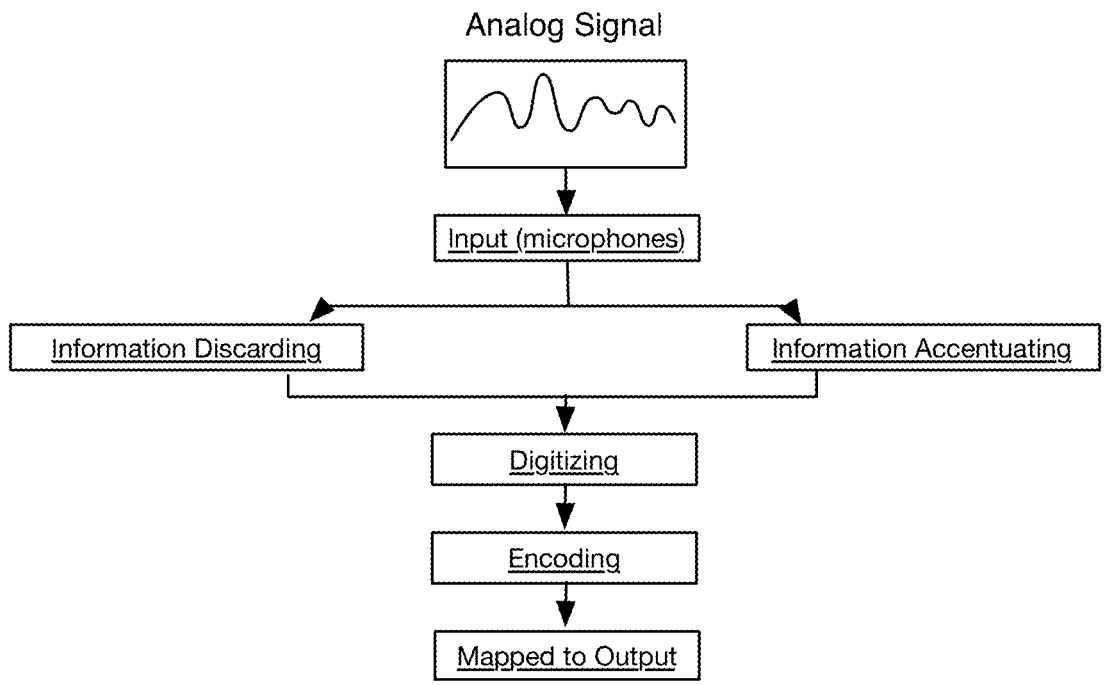
FIGS. 4A-4B depict variations of methods for providing information to a user.
Figure 4B:
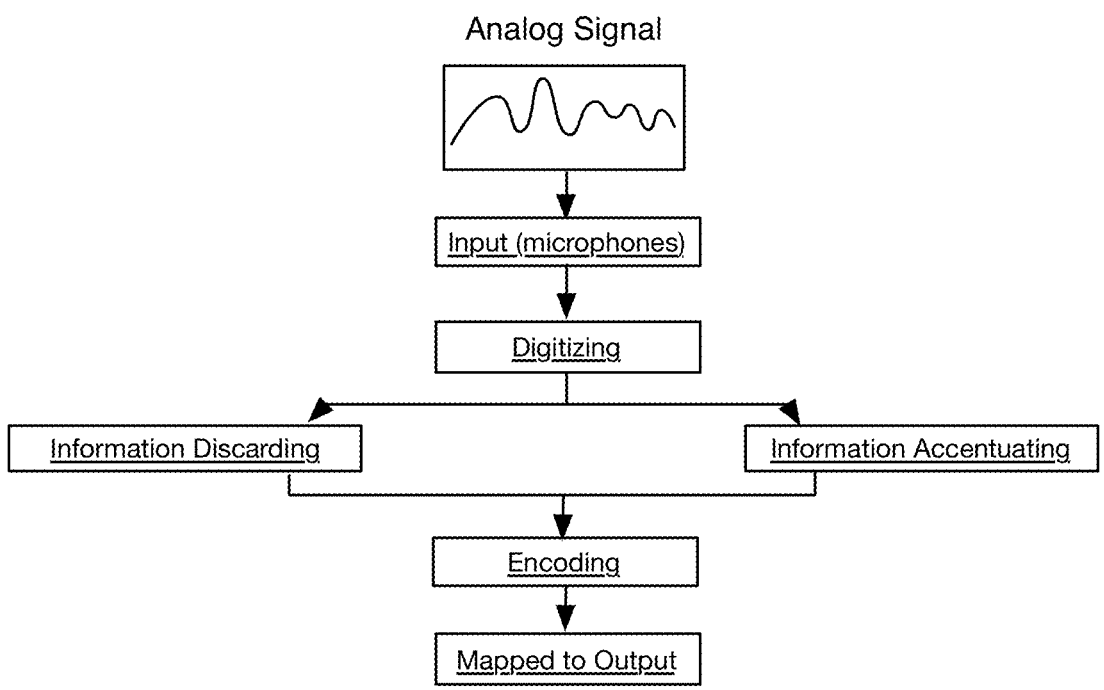

In relation to noise reduction, Block S120 can implement one or more noise reduction techniques including gating operations, expanding operations, operations to remove hum (e.g., in relation to a mains supply frequency and associated harmonics), operations to remove buzz (e.g., in relation to a mains power supply, waveform distortion, and/or harmonics), operations to remove clicks, operations to remove crackle, operations to remove hiss, and any other suitable noise reduction operation. In specific examples, Block S120 can implement one or more of a spectral subtraction operation and an adaptive filtering operation to de-noise incoming audio signals. In variations related to other types of input signals, Block S120 can use any other suitable filtering technique/noise reduction technique. As shown in example FIGS. 4A and 4B, digitizing can occur upstream or downstream of filtering/attenuation operations.

Block S120 can additionally or alternatively implement a separation operation to separate the input signal(s) into multiple signals associated with different sources. In the context of signals capturing speech content, separation can include separating the input signals into a first portion that includes the speech content and at least one other portion that includes non-speech content. In the context of signals capturing environmental audio, separation can include separating the input signals into a first portion associated with a first classification of objects (e.g., transportation-related objects), a second portion associated with a second classification of objects (e.g., pets/animals), a third portion associated with a third classification of objects (e.g., appliances), a fourth portion associated with a fourth classification of objects (e.g., people), and any other suitable number of portions. In the context of signals capturing musical content, separation can include separating the input signals into a first portion that includes a first portion (e.g., associated with melody), a second portion (e.g., associated with vocals), a third portion (e.g., associated with instrumentals), and any other suitable number of portions. Separation operation(s)

associated with any other suitable type(s) of input signal can, however, be implemented in any other suitable manner.

Additionally or alternatively, in some variations, Block S120 can implement a beam forming operation with multiple microphones to remove artifacts (e.g., reverberation artifacts) introduced by the environment of the user. The beam forming operation can include a spatial filtering technique that produces constructive interference of desired signal components (e.g., associated with speech) from multiple sensors (e.g., microphones, accelerometers, etc.), and/or produces destructive interference of undesired signal components (e.g., from the ambient environment) from multiple sensors (e.g., microphones, accelerometers, etc.). The beam forming operation can include control of phasing, relative amplitude and/or any other suitable aspect of signals from each sensor/microphone involved in the process. The beam forming operation can be conventional (e.g., using fixed or switched beam beamformers), or can be adaptive (e.g., using a phased array). The beam forming operation can, however, be implemented in any other suitable manner using any suitable number or type(s) of sensors/microphones.

Block S120 can include implementing a framing operation with the input signal, in order to facilitate latency aspects, and in order to facilitate processing of incoming input signals in an efficient and highly accurate manner. The framing operation can implement any suitable segmenting process to generate frames from the input signal, such that the frames can be processed to identify features of interest (i.e., from Block S130), and/or frames can be labeled accordingly in relation to machine learning operations that improve efficiency of input signal processing for specific user demographics. The frames can be uniformly sized, or can alternatively be non-uniformly sized. Furthermore, the frames can overlap, or alternatively, the frames may not overlap. The method 100 can include performing elements of the method for each frame (e.g., repeating Blocks S110-S160 for each frame), and/or performing analysis on the frames in any other suitable manner. In an example, the framing operation processing a 16 kHz input audio signal into toms frames, wherein the toms frames have 10 ms of overlap with adjacent frames. However, in variations the input signal can have any suitable characteristic frequency, the frames can have any other suitable size, and the frames can have any other suitable overlapped or non-overlapped configuration.

Pre-processing in Block S120 can additionally or alternatively include implementing a windowing operation (e.g., subsequent to the framing operation). In specific examples, the windowing processing includes an AKB window, Hann window, and/or Kaiser window. Pre-processing in Block S120 can additionally or alternatively implement one or more of: zero-padding, normalization, subsampling within frames or across frames, and any other suitable pre-processing step, in order to facilitate downstream processing steps according to the method 100.

Pre-processing in Block S120 can additionally or alternatively include implementing transformation operations (e.g., functional decomposition operations such as Fourier-related transforms) with outputs of the framing operation and/or any other pre-processing steps including one or more of: a discrete cosine transform (DCT) operation, a modified discrete cosine transform (MDCT) operation, a fast Fourier transform (FFT) operation, a discrete Fourier transform (DFT) operation, a Mel-frequency Cepstral Coefficient (MFCC) operation, a wavelet transformation operation, a McAulay-Quatieri (MQ) operation, a Fast Hartley transformation operation, and any other suitable transformation operation, from which features of interest can be extracted in Block S130.

4.3 Extracting Features

Block S130 recites: extracting a set of features from the preprocessed signal, which functions to generate features that can be processed with one or more neural networks, as described in relation to Block S140 below. In more detail, Block S130 extracts features from the pre-processing operation, which can be provided to the neural network systems of Block S140 to generate or facilitate recognition of components of the input signal efficiently, for eventual encoding and mapping to haptic device outputs. Block S130 is preferably implemented at the processing system components in communication or otherwise coupled to the sensor components associated with Block S110 and described in Section 3 above; however, Block S130 can additionally or alternatively be implemented using any other suitable system components.

In the context of speech information from the input signals, Blocks S130 and S140 can facilitate generation of features that can ultimately be used for transmitting of information from speech components (e.g., phonemes, words, senones, subphones, diphones, triphones, quinphones, utterances, fillers, etc.) to be perceived by the user in Blocks S150 and S160. However, in the context of other input signals, Blocks S130 and S140 can be used for recognition of any other suitable information components from the input signal(s), for transmission of appropriate stimuli to users in Blocks S150 and S160.

Block S130 can include generating derived features associated with spectral/frequency from the pre-processing operations of Block S120. In variations, derived features can be associated with one or more of: spectral peak frequencies, spectral peak magnitudes, spectral rolloff aspects, spectral centroid aspects, frequency band features (e.g., energy ratios), gammatone transforms (e.g., gammatone transform coefficients), measures of spectral deformation, measures of spectral width, zero-crossing features (e.g., zero crossing rates), moments of crossing intervals, lacunarity, whitening transforms (e.g., elements of a whitening transform matrix), and any other suitable derived features.

Additionally or alternatively, Block S130 can include generation of any other suitable features, in relation to any other suitable input signal type and/or encoded information associated with the stimuli provided in subsequent blocks of the method 100.

4.4 Neural Network Operations

Block S140 recites: processing the set of features with a neural network system, which functions to transform the features of Block S130 into outputs that can be encoded and mapped in a manner for provision of stimuli to the user as described in relation to Blocks S150 and S160 below. Block S140 is preferably implemented at the processing system components described in Section 3 above. In one variation, Block S140 is implemented on embedded hardware (e.g., of the stimulation device, of the device(s) including sensors for generation of the input signals) and/or on a mobile computing device in communication with one or more devices of the system, etc.), with or without supplemental digital signal processors (DSPs). However, Block S130 can additionally or alternatively be implemented using any other suitable system components.

Figure 5:
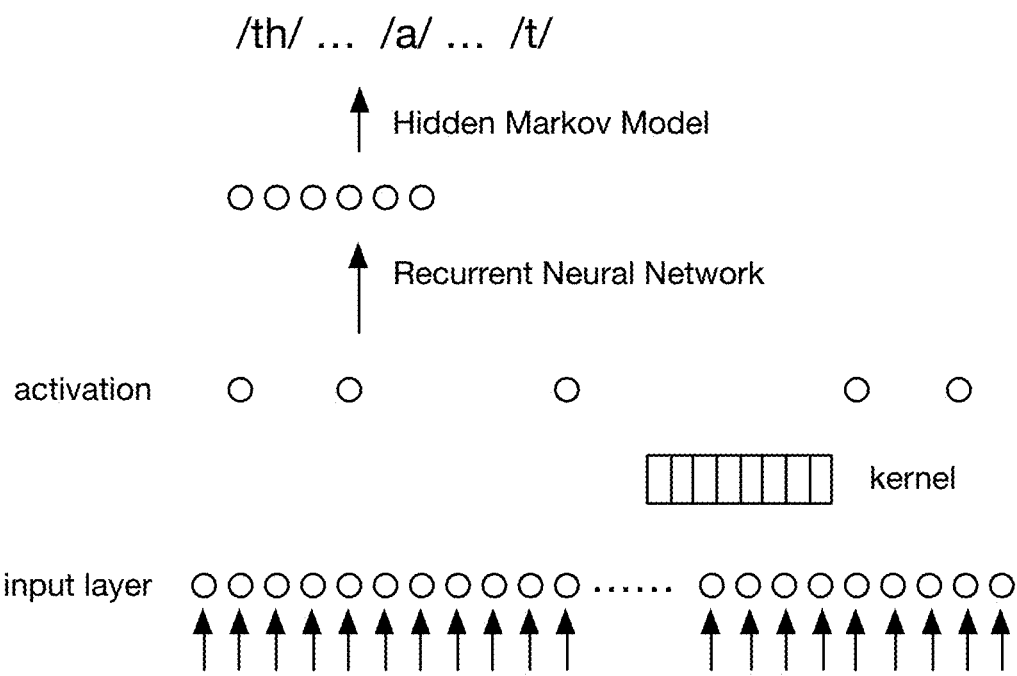
FIG. 5 depicts an example of a neural network architecture associated with a method for providing information to a user.

In Block S140, the neural network operations can include one or more of fully connected configurations, convolutional configurations, and recurrent configurations, combinations of multiple network configurations (e.g., as in batch normalization designs, skip connection designs, multiplicative integration designs, etc.). In variations, the neural network(s) implemented in Block S140 can include one or more of: recurrent neural networks (e.g., with a long short term memory design, with a gated recurrent unit design, etc.), convolutional neural networks, feedfoward neural networks, deep neural networks, and any other suitable variant of neural network. Additionally or alternatively, the neural network(s) implemented in Block S140 can be supplemented with statistical models for reinforcement learning and pattern recognition of components of interest from input signals, wherein such statistical models can include one or more of: Hidden Markov Models (HMMs), language models, mixture models (e.g., Gaussian mixture models), and/or any other suitable statistical models. In a specific example, represented in FIG. 5, Block S140 can implement a convolutional neural network with a convolutional layer having a dimension smaller than that of the input layer, with a recurrent neural network design and a Hidden Markov Model for learning/recognizing speech components (e.g., phonemes, words, senones, subphones, diphones, triphones, quinphones, utterances, fillers, etc.). In relation to the specific example, the neural networks can include additional inputs to any layer and/or modification of weights associated with network components. Additionally or alternatively, the neural networks can incorporate one or more of: a network selector, a volume normalizer, information from additional sensors for learning of a noise environment associated with the input signal(s), and any other suitable data/information.

In relation to additional sensors to enhance learning and recognition facilitated by the neural network(s), Block S140 can leverage data from one or more of: motion sensors (e.g., accelerometers, gyroscopes) for beam forming to learn signal source aspects; location identifying modules (e.g., GPS systems) for selecting networks (e.g., localizing to accents associated with speech content); barometers for learning environmental pressure characteristics; light sensors for learning environmental light characteristics; temperature sensors for learning environmental temperature characteristics; air flow meters; current sensors (e.g., Hall effect sensor); voltmeters, touch sensors (e.g., resistive, capacitive, etc.); proximity sensors; force sensors (e.g., strain gauge meter, load cell); vibration sensors; chemical sensors; and/or any other suitable sensors for learning signal components associated with speech content, the environment of the user, and/or any other suitable input signal components.

The neural networks can be trained (e.g., with dropout and stochastic gradient-based techniques), and in specific examples, can be trained using one or more of: Adam-based methods for efficient stochastic optimization with first-order gradients; second order quasi-Newton methods (e.g., Broyden-Fletcher-Goldfarb-Shanno methods, limited-memory Broyden-Fletcher-Goldfarb-Shanno methods, KFAC methods, etc.), and other methods (e.g., gradient descent methods, Newton's method, conjugate gradient methods, Levenberg-Marquardt methods, etc.). Training data can be augmented with features of the input signal(s), wherein the features can be derived or learned. In examples, the training data features can include or be derived from one or more of: spectral peak frequencies, spectral peak magnitudes, spectral rolloff aspects, spectral centroid aspects, frequency band features (e.g., energy ratios), gammatone transforms (e.g., gammatone transform coefficients), measures of spectral deformation, measures of spectral width, zero-crossing features (e.g., zero crossing rates), moments of crossing intervals, lacunarity, whitening transforms (e.g., elements of a whitening transform matrix), and any other suitable derived features.

In relation to network configurations, Block S140 can implement compression techniques (e.g., in order to allow such neural networks to run efficiently without supplemental signal processing hardware, as indicated above). Network compression techniques can include one or more of: binarization of weights, trained quantization, Huffman coding, pruning, hashing to exploit redundancy in neural networks to achieve reductions in model sizes, and any other suitable compression technique. In a specific example, compression of the neural network(s) used in Block S140 involves a deep compression process including pruning, trained quantization, and Huffman coding to reduce storage requirements without affecting accuracy. Such a method provides increased efficiency and speed in processing, and increases flexibility in where such neural network(s) can be run.

In variations of the method 100 for speech recognition, encoding, and mapping, outputs of the neural networks can include frames labeled with speech component features associated with one or more of: phonemes, sub-phoneme components, super-phoneme assemblies, non-phoneme components (e.g., phones, diphones, triphones, diphthongs, triphthongs, etc.), words, sentences, and/or any other suitable language components. In related to derived features, outputs can include frame-wise probabilities of speech components identified, accuracy metrics associated with identified speech components, and any other suitable derived features (which can be processed in a machine learning feedback loop, described in more detail in Section 4.6 below). Outputs of the neural networks can additionally or alternatively include features of environmental objects (e.g., motion characteristics, morphological characteristics, classification aspects, state characteristics), features associated with indications of hazards to the user, features associated with other environmental information (e.g., in relation to changes in environmental states that may not be associated with hazards), and any other suitable features. Outputs of the neural networks can additionally or alternatively include any other suitable neural network outputs.

Block S140 can additionally or alternatively include other feature—output transformation techniques (e.g., not using neural networks)

4.5 Mapping and Producing Haptic Outputs 4.5.1 Encoding and Mapping

Block S150 recites: mapping outputs of the neural network system to a device domain associated with a device including a distribution of haptic actuators in proximity to the user. Block S150 functions to encode and map feature- and/or parameter value-derived outputs of the neural network system of Block S140, for use in controlling outputs of the stimulation devices of Block S160. As such, Block S150 facilitates transformation of speech component outputs (or other outputs associated with input signals) from the neural network system of Block S140, into stimuli that can be delivered to the user at a device in proximity to the user.

In specific examples, Block S150 preferably includes encoding and mapping of speech components (e.g., frequency coefficient amplitudes, peak frequency values, phonemes, words, etc.) to specific device elements and/or stimulation parameters. Mappings between speech components (or other components of interest extracted from the input signals) can be associated with actuators of the array of tactile interface devices in a 1:1 manner or alternatively, not in a 1:1 manner. As such, Block S150 can include encoding and/or mapping complex waveforms associated with stimulation parameters of a subset of the array of tactile stimulation devices (e.g., to create stimulation "textures" associated with different components of interest). However, Block S150 can include encoding and/or mapping in any other suitable manner.

In one variation, Block S150 encodes the outputs of the neural network system of Block S140 to haptic patterns executable using the array of tactile interface devices described in Section 3 above, wherein the haptic patterns are associated with control signals that activate devices of the array of tactile interface devices, and wherein the control signals can be executed in Block S160 of the method 100. In variations of Block S150 associated with speech component-associated outputs, Block S150 can include can encoding each of the outputs with a spatial aspect and/or device stimulation parameter of the array of tactile interface devices. In relation to speech components described, the Block S150 can transform, encode, or otherwise map outputs derived from the neural network operation(s) of Block S140 to one or more of: subdomains (e.g., subregions, sub-clusters, sublayers, etc.) of the array of tactile interface devices; different stimulus aspects associated with the array of tactile interface devices; and any other suitable aspects of the array of tactile stimulus devices.

Figure 6:
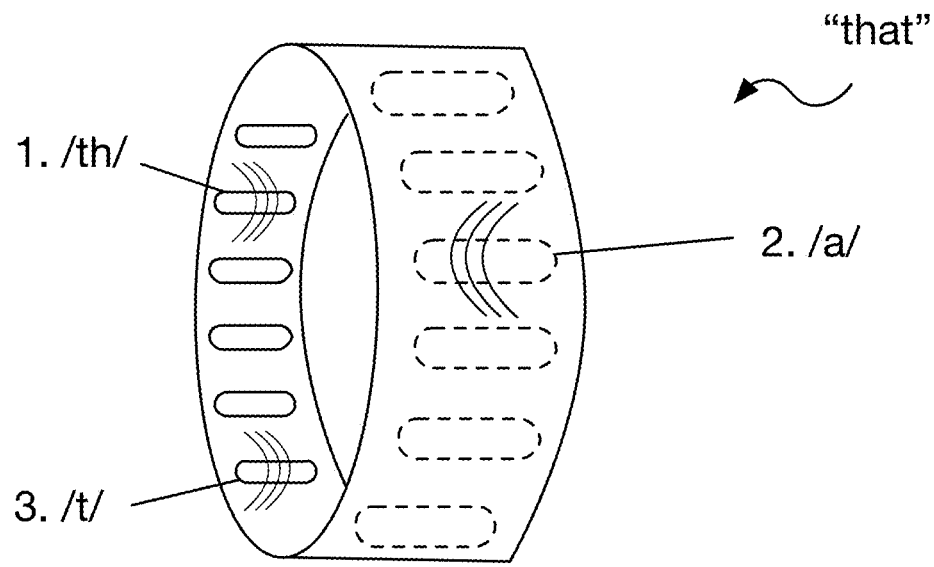
FIG. 6 depicts an example of a haptic output representative of speech content information in an embodiment of a method for providing information to a user.

Speech components of Block S140 can be mapped to domains (e.g., layers, regions, clusters, areas, etc.) of the array of tactile interface devices, examples of which are shown in FIG. 6. As such, different speech components (e.g., frequency locations of formants, peak frequency amplitudes, phonemes, sub-phoneme components, super-phoneme assemblies, phones, diphones, triphones, diphthongs, triphthongs, etc.) can be mapped to different domains of the array of tactile interface devices. For instance, in a device variation that has a distribution of the array of tactile stimulation devices configured about a wristband wearable: each device of the array of tactile stimulation devices can be associated with a corresponding phoneme or word, such that different devices of the array of tactile stimulation devices can "play" phonemes/words in a specific pattern that corresponds to the message of the communication data of Block S110, and can be detected at a wrist region of the user.

In another example, in a device variation that has a distribution of the array of tactile stimulation devices integrated with a wearable system or other support system in proximity to the user: each device of the array of tactile stimulation devices can be associated with a corresponding phoneme or word, such that different devices of the array of tactile stimulation devices can "play" phonemes/words in a specific pattern that corresponds to the message of the communication data of Block S110, and can be detected at a body region of the user that is receptive to touch sensations. However, variations of the example can associate devices of the array of tactile stimulation devices with speech components in any other suitable manner.

In the examples and variations described above, the domains/regions of the array of tactile stimulation devices can be fixed or dynamically modifiable. For instance, the subdomain can be dynamically modified, according to the encodings performed in Block S150, in order to convey a wider variety of information and/or more complex information to the user with a limited physical device space.

Additionally or alternatively, in variations related to speech components described in Block S140 above, the transformation model can additionally or alternatively transform, encode, or otherwise associate speech component labels with a set with stimulus parameters of the array of tactile interface devices. In variations, the transformation operation can map different speech components (e.g., phoneme pitch, phoneme energy, phoneme tone, phoneme emphasis, etc.) to a range of stimulus types. In variations, stimulus parameters can include one or more of: output type (e.g., intermittent, pulsed, continuous, etc.); pulse pattern; pulse waveform characteristics (e.g., sinusoidal, square wave, triangular wave, wavelength, etc.), output amplitude, output intensity; output duration; out pulse duration, etc.), device domains involved in an output (e.g., a sweeping pattern using multiple devices), and any other suitable stimulus parameter. For instance, in a device variation that has a distribution of the array of tactile stimulation devices configured about a wristband wearable: each device of the array of tactile stimulation devices can output a specific stimulus parameter corresponding to a speech component, such that the devices can relay information not only to speech component labels (e.g., phoneme labels), but also more complex language aspects (e.g., phoneme pitch, phoneme energy, phoneme tones, phoneme emphasis, etc.) and can be detected at a wrist region of the user.

In another example, in a device variation that has a distribution of the array of tactile stimulation devices integrated with a wearable device or other support structure in proximity to the user: each device of the array of tactile stimulation devices can output a specific stimulus parameter corresponding to a speech component, such that the devices can relay information not only to speech component labels (e.g., phoneme labels), but also more complex language aspects (e.g., phoneme tones, phoneme emphasis, etc.) and can be detected at a body region of the user that is sensitive to touch. However, variations of the example can associate stimulus parameters of the array of tactile stimulation devices with speech components in any other suitable manner.

In variations related to speech components described in Block S140 above, the transformation model can additionally or alternatively transform, encode, or otherwise associate speech component outputs of Block S140 with complex or combined outputs of the array of tactile interface devices. In variations, the transformation operation can result in generation of encodings related to both subdomains and stimulus outputs available using the array of tactile stimulus devices.

In a first example, associated with the English language, the Block S150 can assign each of 47 phoneme labels to specific devices of the array of tactile interface devices (e.g., distributed about a wristband, distributed across a vest, etc.), such that the array of tactile interface devices can "play back" stimuli associated with different phonemes in an order corresponding to portions of the input signal(s) received in Block Silo. As shown in FIG. 6, a wrist band can include an array of tactile interface devices, each mapped to a specific phoneme, which can be signaled to play the phoneme according to a pattern corresponding to the input signals in Block S110. In a second example, associated with spoken Mandarin, Block S150 can assign each of 41 phoneme labels to specific devices of the array of tactile interface devices and four stimulus patterns (e.g., pulse patterns) associated with four spoken tones, such that the array of tactile interface devices can "play back" stimuli associated with different phonemes and different phoneme tones in an order corresponding to portions of the input signals(s) received in Block S110.

Encoding and mapping in Block S150 can additionally or alternatively be implemented in any other suitable manner, such as described in U.S. application Ser. No. 14/750,626, titled "Providing Information to a User Through Somatosensory Feedback" and filed on 25 Jun. 2015.

4.5.2 Stimulation Delivery

Block S160 recites: at the distribution of haptic actuators, cooperatively producing a haptic output representative of at least a portion of the input signal, thereby providing information to the user. Block S160 preferably includes executing control signals operable to deliver stimulation through the array of tactile interface devices (e.g., the output parameters determined in Block S150, etc.) with the distribution of tactile interface devices coupled to the user. Block S150 preferably functions to enable outputs to be delivered to the user through the tactile interface devices, according to the transformation and encoding algorithms of Blocks S120-S140. The control signals can be executed according to methods described in U.S. application Ser. No. 14/750,626, titled "Providing Information to a User Through Somatosensory Feedback"; however, the control signals can additionally or alternatively be executed in any other suitable manner. For instance, Block S160 can include receiving one or more user inputs operable to adjust a gain level, equalizer levels, and/or other aspect(s) of output stimuli, such that the user can customize the intensity of stimuli provided through the array of tactile interface devices (e.g., of all stimuli, of stimuli associated with particular input and/or output characteristics, etc.). However, Block S150 can additionally or alternatively include controlling the output devices in any other suitable manner.

Figure 7:
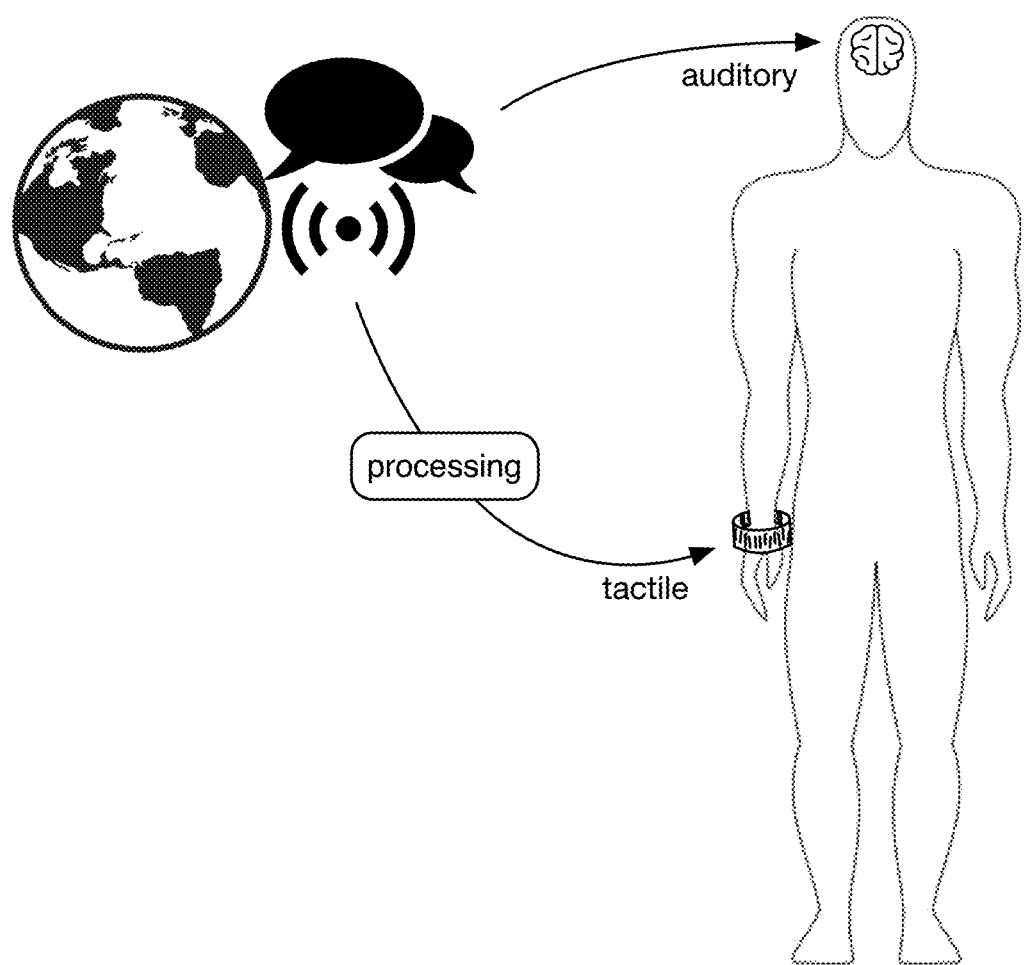
FIG. 7 depicts a portion of a method for providing information to a user.

In the variations and examples described above, phoneme outputs generated in Block S140 and corresponding to the input signal(s) of Block S110 can be encoded, mapped, and delivered through the array of tactile interface devices in a manner similar to the natural timing of speech. In more detail, stimulus provision in Block S160 preferably occurs in real-time or near real-time (e.g., within a time threshold, such as 100 ms, 90 ms, 75 ms, 50 ms, 110 ms, 125 ms, 150 ms, 200 ms, 300 ms, etc.), as represented in FIG. 7, such that the user perceives tactile feedback substantially simultaneously with reception of input signals in Block S110 (e.g., is unable to discern a delay between the input signal and tactile feedback), with minimal delay. However, delivery of haptic stimuli can alternatively be implemented in a manner that does not mimic natural speech timing. As such, delivery of haptic stimuli can be implemented with any suitable speed, frequency, cadence, pauses (e.g., associated with grammatical components of language), gain (e.g., amplitude of stimulation corresponding to "loudness" or punctuation), pattern (e.g., spatiotemporal pattern played using subarrays of the array of tactile interface devices, etc.), and any other suitable output component.

Stimulus provision in Block S160 can, however, be implemented in any other suitable manner.

4.6 Additional Machine Learning Aspects and Feedback Loops

While neural network operations are described in Block S140 above, the method 100 can additionally or alternatively implement additional or alternative machine learning techniques for optimization of extraction of speech components or other components from the input signal. The method 100 can additionally or alternatively implement machine learning algorithms having an objective function for optimizing power consumption of the array of tactile interface devices, thereby improving overall device and/or system performance. Additionally or alternatively, machine learning algorithms can be used to optimize stimulation outputs for user specific conditions (e.g., user specific hearing loss), as described in more detail below.

In one variation, given N tactile interface devices in the array of tactile interface devices and one-hot encoding of speech components (e.g., phonemes), N+1 classes can be represented (including a "BLANK" state associated with inactivation of all of the array of tactile interface devices). In this variation, an objective function for machine learning operations can include an optimization of frame-wise cross-entropy among predicted speech component (e.g., phoneme) annotations; however, optimization of parameters in relation to frames of input signal data can be implemented in any other suitable manner. Additionally or alternatively, an objective can include generation of accuracy metrics associated with speech component annotations, wherein in a specific example, log-likelihoods of a phoneme-level accuracy metric can be determined across a set of contiguous frames of input signal data, based on an analysis of correct annotation for each of the set of frames. In more detail, an entire phoneme captured in the set of frames of input signal data can exhibit a high level of the accuracy metric if every frame is predicted to be either correct or BLANK, and at least one frame is predicted to be correct. Such accuracy analyses can then be used to refine annotations of phoneme (or other speech components) in processing subsequent frames of input signal data. Additionally or alternatively, accuracy analyses can be used to modulate stimulus output aspects of the array of tactile interface devices, in relation to Block S160 above. For instance, tactile feedback can be scaled to represent accuracy level in relation to predictions of phonemes in frames of the input signal data. Generation and usage of accuracy metrics for optimization can, however, be implemented in any other suitable manner.

Additionally or alternatively, in some variations, an objective function for machine learning operations can include optimization of power consumption characteristics associated with the array of tactile interface devices (e.g., in relation to specific device constraints). In one specific example, such operations can optimize for sparsity of an encoded representation of a speech component output with respect to delivery of stimulus parameters upon activation of one or more of the array of tactile interface devices, wherein sparsity is optimized to reduce power consumption while still allowing perception of the stimuli by the user. In relation to these variations, a dynamic range of motor activations can be learned from psychophysical analyses of users (e.g., with respect to minimum sensory perception thresholds, with respect to maximum sensory perception thresholds); however, optimizing power consumption under a constraint of stimuli perception by a user can be implemented in any other suitable manner.

Figure 8A:
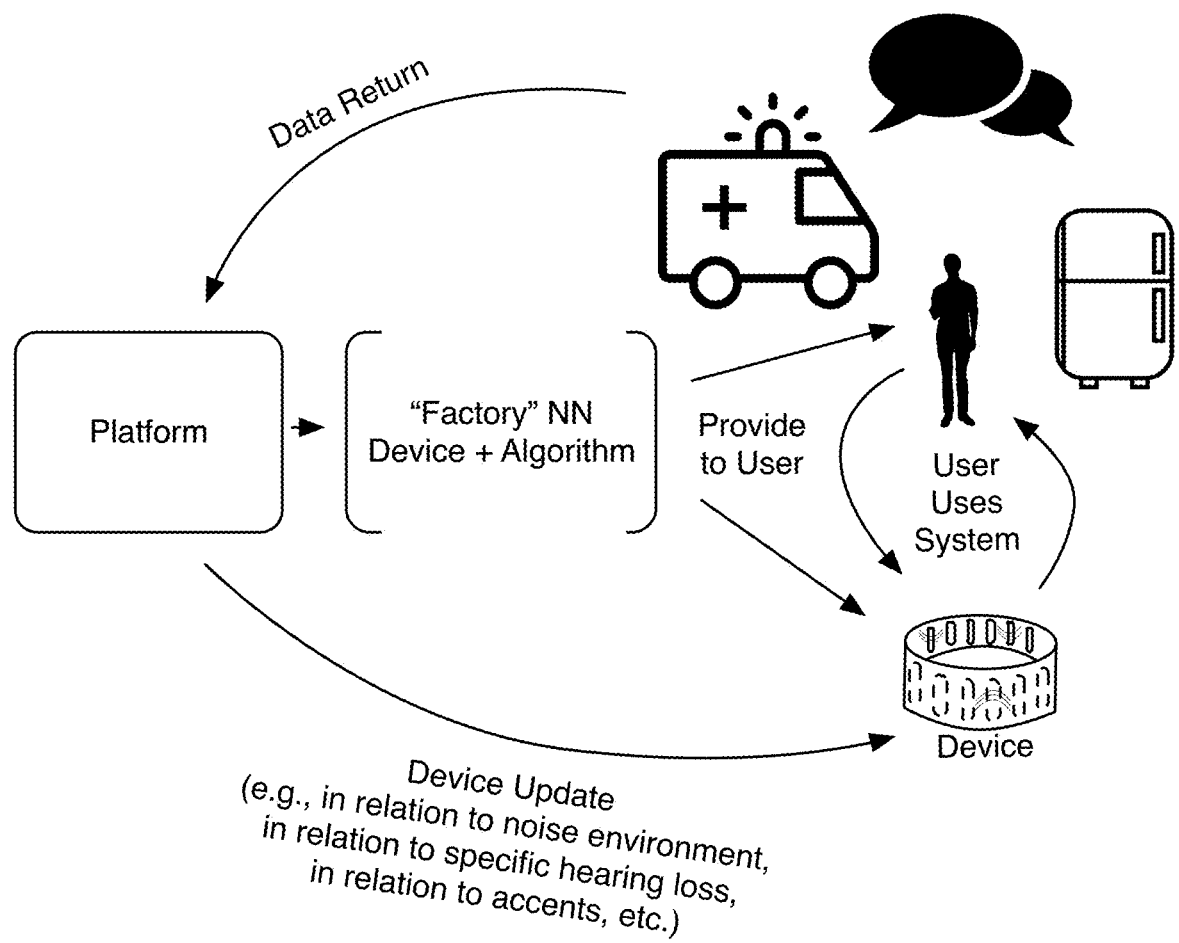
FIGS. 8A-8B depict variations of method flows involving machine-learning facilitate system updates for improving provision of information to a user.
Figure 8B:
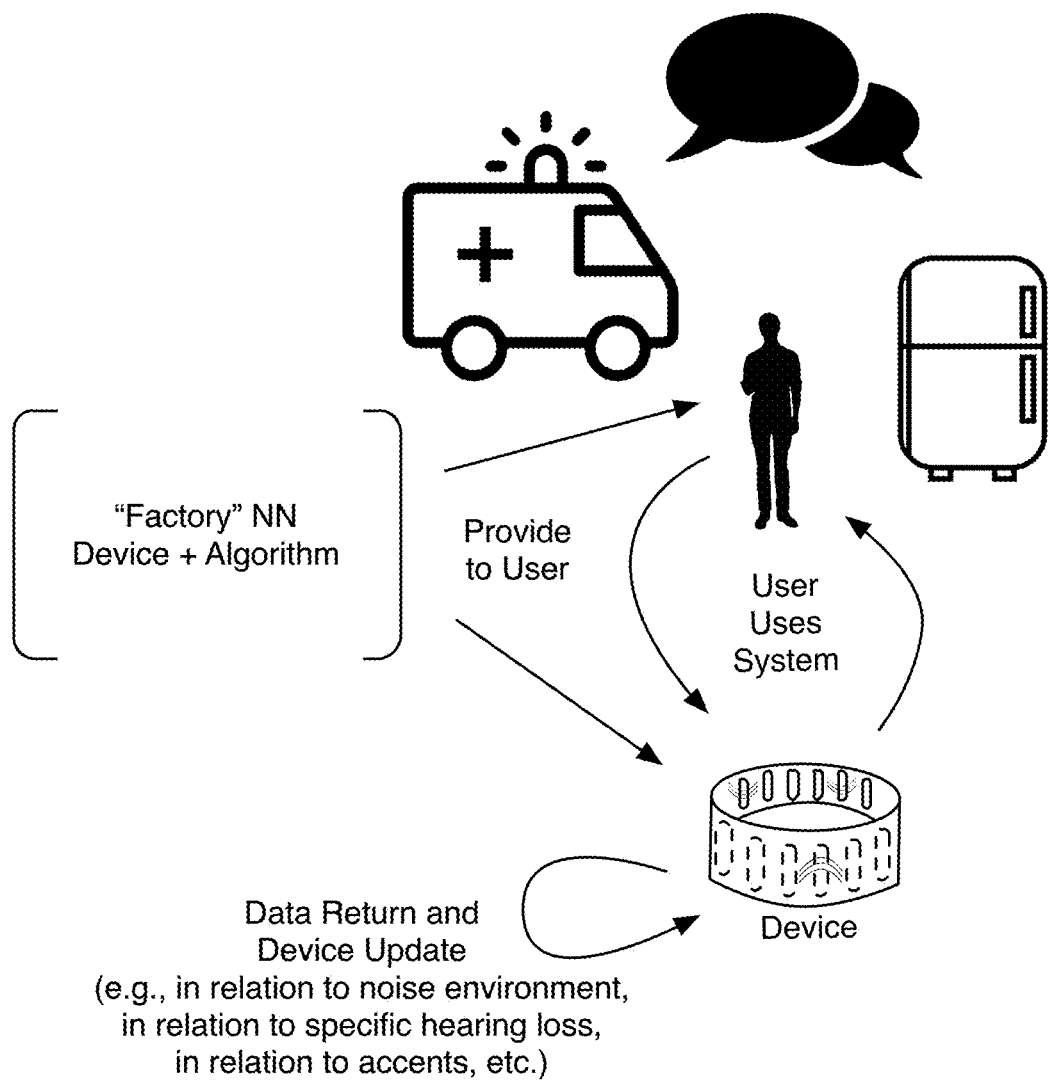

Additionally or alternatively, in relation to optimization of stimulation delivery for specific user or environment conditions (e.g., in relation to user specific hearing loss, in relation to noise environments, in relation to accents, etc.), an example method flow is shown in FIG. 8A. In more detail, an original system state (e.g., in "factory" conditions) including a device (e.g., wristband) and original-state neural network-based algorithm can be provided to a user. Then, as the user uses the device according to his/her conditions and in his/her environment, data gathered during use can be transmitted back to remote processors (e.g., of a cloud-based system for aggregating and processing user data) to update the original-state neural network-based algorithm to a user data-informed algorithm. The device (e.g., wristband) can then be updated (e.g., in a remote firmware update operation) and the cycle can continue as the user continues to use the device. In an alternative configuration, as shown in FIG.

8B, the remote processors can be omitted, and the device can be configured to update itself as the user uses the device.

Furthermore, the method 100 can include any other suitable Blocks operable to promote provision of information to users, through the array of tactile interface devices, in any other suitable manner. For instance, the method 100 can include rapidly training a user to learn to correctly identify speech components associated with haptic outputs provided through an array of tactile interface devices, by providing pre-recorded speech with time-locked haptic outputs through the array of tactile interface devices. In a specific application, such a training protocol can allow users with high-frequency hearing loss to help them discriminate between commonly confused higher frequency phonemes (e.g., /th/, /f/, /s/, /h/, /k/, /z/, /b/, /dh/, /t/, /d/, /v/, etc.), in coordination with stimulus provision through the array of tactile interface devices. For example, the method can include providing haptic outputs (e.g., at the array of tactile interface devices) representing phoneme components related to phonemes that users with high-frequency hearing loss (e.g., presbycusis) may have difficulty perceiving. In a first specific example, the method includes providing haptic outputs representing phoneme components (e.g., high frequency phoneme components) including /f/, /z/, /b/, /th/, /dh/, /t/, /d/, /s/, and/or /v/. In a second specific example, the method includes providing haptic outputs representing phoneme components (e.g., high frequency phoneme components) including /th/, /f/, /s/, /h/, and/or /k/. However, variations of the training protocol can alternatively be implemented for users with other impairments, users with no impairments, and/or for any other suitable phonemes or speech components.

While some variations of machine learning techniques are described above, in relation to steps of the method 100 above, the method 100 can additionally or alternatively utilize any other suitable machine learning algorithms. In variations, the machine learning algorithm(s) can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the machine learning algorithm can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial least squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm.

4.7 Alternative Feature—Output Transformations.

The method 100 can additionally or alternatively include other feature—output transformation techniques (e.g., not using neural networks, supplementing the neural network techniques described above regarding Block S140, etc.). In one such variation, the method includes transforming frequency-related features of the input signal into output signals.

A first example of this variation includes: segmenting the input signal into windows (e.g., as described above regarding Block S110) and, for each window: performing a transformation (e.g., DCT and/or other functional decomposition, such as described above regarding Block S120); optionally discarding extraneous portions of the transformation output (e.g., for a user with high-frequency hearing loss, discarding DCT coefficients corresponding to lower-frequency input signal features, such as frequencies easily perceived by the user); and mapping the remaining (e.g., not discarded) transformation outputs (e.g., DCT coefficient magnitudes) to actuator outputs (e.g., as described above regarding Block S150). This example can optionally include performing a dimensionality reduction procedure. For example, if the number of remaining DCT coefficients is greater than the number of haptic output devices, the coefficients can be binned (e.g., into larger frequency bands), and the average magnitude of the coefficients in each bin can be mapped to actuator outputs. The binning can be uniform or non-uniform (e.g., pre-determined and/or dynamically-determined binning; determined based on individual user needs, typical preferences, etc.).

A second example of this variation includes: optionally performing a time-domain filtering of the input signal to discard extraneous frequencies (e.g., for a user with high-frequency hearing loss, using a high-pass filter to discard lower-frequencies of the input signal, such as frequencies easily perceived by the user); extracting a plurality of frequency bands (e.g., one for each actuator or controlled subset) from the filtered input signal (e.g., performing parallel bandpass filtering processes on the signal); determining a metric associated with each band (e.g., the envelope of each band); and mapping this metric to actuator outputs. The frequency bands extracted for the actuators are preferably contiguous frequency ranges, but can additionally or alternatively include any suitable frequency bands.

However, the method 100 can additionally or alternatively include any other suitable feature—output transformation techniques.

4.8 Repetition.

The method 100 can optionally include repeating any or all of the method blocks (e.g., Blocks S110-S160). In one example, the method 100 include receiving a continuous stream of input information (e.g., real-time audio signals, such as sampled at the microphone systems of the device) in Block S110, and continuously performing Blocks S110-S160 based on the input information (e.g., based on a recently-received subset of the information). In a second example, the method 100 includes receiving bulk input information in Block S110, segmenting the input information into consecutive time windows, and performing Blocks S120-S160 for each time window. However, the method 100 and/or any of its elements can be repeated in any other suitable manner.

Although omitted for conciseness, the preferred embodiments include every combination and permutation of the various system components and the various method processes. Furthermore, various processes of the preferred method can be embodied and/or implemented at least in part as a machine configured to receive a computer-readable medium storing computer-readable instructions. The instructions are preferably executed by computer-executable components preferably integrated with the system. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processing subsystem, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A system for providing information to a user, the system comprising:
   a limb-worn device comprising an audio sensing device, wherein the audio sensing device receives an audio signal from an environment of the user;
   a processing system, wherein the processing system:
      processes the audio signal with a trained neural network model to determine a set of outputs;
      maps the set of outputs to a set of tactile actuators arranged onboard the limb-worn device; and
   the set of tactile actuators, wherein the set of tactile actuators cooperatively produces tactile sensation representative of the audio signal, thereby conveying information associated with the audio signal to the user at the limb-worn device.

2. The system of claim 1, wherein the processing system is arranged onboard the limb-worn device.

3. The system of claim 2, wherein the audio sensing device is a single microphone arranged onboard the limb-worn device.

4. The system of claim 1, wherein mapping the set of outputs to the set of tactile actuators comprises mapping the set of outputs to a device domain associated with an arrangement of the set of tactile actuators.

5. The method of claim 4, wherein the set of outputs comprises a set of phonemes, and wherein mapping the set of phonemes to the device domain comprises mapping multiple phonemes to a single tactile actuator of the set of tactile actuators.

6. The method of claim 1, wherein the audio signal comprises high frequency audio, and wherein the trained model is configured to identify the high frequency audio.

7. The method of claim 6, wherein the set of outputs comprises a set of high frequency phonemes.

8. The method of claim 7, wherein the trained neural network model is configured to detect high frequency phonemes corresponding to speech, wherein the set of high frequency phonemes includes only the high frequency phonemes corresponding to speech.

9. The method of claim 1, wherein the trained neural network model comprises a recurrent neural network.

10. The method of claim 9, wherein the trained neural network model further comprises a Hidden Markov Model.

11. The method of claim 1, wherein the set of tactile actuators comprises a plurality of tactile actuators, wherein the plurality of tactile actuators is arranged circumferentially about a band support structure of the limb-worn device, the band support structure operable to be positioned at a limb of the user.

12. A method for providing information to a user, the method comprising:
   with a limb-worn device comprising an audio sensing device and a set of tactile actuators, receiving an audio signal at the audio sensing device from an environment of the user;
   at a processing system in communication with the limb-worn device:
      processing the audio signal with a trained neural network model to determine set of outputs;
      mapping the set of outputs to the set of tactile actuators; and
   with the set of tactile actuators, cooperatively producing tactile sensation representative of the audio signal, thereby conveying information associated with the audio signal to the user at the limb-worn device.

13. The method of claim 12, wherein the trained neural network model comprises a recurrent neural network architecture and implements a statistical model for recognition of speech components from the audio signal.

14. The method of claim 13, wherein trained neural network model further comprises a convolutional layer.

15. The method of claim 12, wherein mapping the set of outputs to the set of tactile actuators comprises mapping the set of outputs to a device domain associated with an arrangement of the set of tactile actuators.

16. The method of claim 15, wherein the set of outputs comprises a set of phonemes, and wherein mapping the set of phonemes to the device domain comprises mapping multiple phonemes to a single tactile actuator of the set of tactile actuators.

17. The method of claim 12, wherein the audio signal comprises high frequency audio, and wherein the trained model is configured to identify the high frequency audio.

18. The method of claim 17, wherein the set of outputs comprises a set of high frequency phonemes.

19. The method of claim 18, wherein the trained neural network model is configured to detect high frequency phonemes corresponding to speech, wherein the set of high frequency phonemes is only high frequency phonemes corresponding to speech.

20. The method of claim 12, wherein the audio sensing device is a single microphone arranged onboard the limb-worn device.

* * * * *